(12) United States Patent
Orning et al.

(10) Patent No.: US 8,802,382 B2
(45) Date of Patent: Aug. 12, 2014

(54) COBALAMIN ASSAY

(71) Applicant: Axis-Shield ASA, Oslo (NO)

(72) Inventors: Lars Orning, Oslo (NO); Anne Rian, Oslo (NO)

(73) Assignee: Axis-Shield ASA, Oslo (NO)

( * ) Notice: Subject to any disclaimer, the term of this patent is extended or adjusted under 35 U.S.C. 154(b) by 0 days.

(21) Appl. No.: 14/138,217

(22) Filed: Dec. 23, 2013

(65) Prior Publication Data

US 2014/0147868 A1 May 29, 2014

Related U.S. Application Data

(62) Division of application No. 12/611,455, filed on Nov. 3, 2009, now Pat. No. 8,647,831, which is a division of application No. 10/536,327, filed as application No. PCT/GB03/05167 on Nov. 26, 2003, now Pat. No. 7,632,648.

(30) Foreign Application Priority Data

| Nov. 26, 2002 | (GB) | .................................... 0227544.4 |
| Dec. 9, 2002 | (GB) | .................................... 0228674.8 |
| Apr. 3, 2003 | (GB) | .................................... 0307727.8 |

(51) Int. Cl.
*G01N 31/00* (2006.01)
*G01N 33/53* (2006.01)

(52) U.S. Cl.
USPC .......... 435/7.21; 435/7.1; 435/7.23; 436/501; 436/518; 422/430; 424/130.1; 530/300; 530/350

(58) Field of Classification Search
CPC .... C07K 16/18; C07K 16/44; C07K 2317/32; G01N 33/5735

See application file for complete search history.

(56) References Cited

U.S. PATENT DOCUMENTS 7,632,648 B2 * 12/2009 Orning et al. .................. 435/7.1
8,647,831 B2 * 2/2014 Orning et al. ................ 435/7.21

FOREIGN PATENT DOCUMENTS

| WO | WO 01/17659 A | * | 3/2001 | ............ B01D 33/00 |
| WO | WO 01/63297 A | * | 8/2001 | ............ G01N 33/82 |
| WO | WO 02/086513 A | * | 10/2002 | ........... G01N 33/573 |
| WO | WO 02/086513 A2 | * | 10/2002 | ........... G01N 33/573 |

OTHER PUBLICATIONS

Ulleland M. et al., "Direct Assay for Cobalamin Bound to Transcobalamin (Holo-Transcobalamin) in Serum," Clinical Chemistry, American Association for Clinical Chemistry, Winston, US, vol. 48, No. 3, Mar. 2002, 526-532, XP001145417.*
Yamada et al., Kidney International, vol. 39, 1991, 289-294.*

* cited by examiner

*Primary Examiner* — Lisa Cook
(74) *Attorney, Agent, or Firm* — Bacon & Thomas, PLLC

(57) ABSTRACT

The present invention provides a specific binding partner for holoTC having a specificity for holoTC over apoTC of at least 40-fold and an assay method for assaying for holoTC in a sample, the method comprising contacting the sample with a specific binding partner for holoTC and detecting the resultant conjugates.

13 Claims, 13 Drawing Sheets

SEQUENCE LISTING

<160> NUMBER OF SEQ ID NOS: 19

<210> SEQ ID NO 1
<211> LENGTH: 427
<212> TYPE: PRT
<213> ORGANISM: Homo sapiens

<400> SEQUENCE: 1

```
Met Arg His Leu Gly Ala Phe Leu Phe Leu Leu Gly Val Leu Gly Ala
1               5                   10                  15

Leu Thr Glu Met Cys Glu Ile Pro Glu Met Asp Ser His Leu Val Glu
            20                  25                  30

Lys Leu Gly Gln His Leu Leu Pro Trp Met Asp Arg Leu Ser Leu Glu
        35                  40                  45

His Leu Asn Pro Ser Ile Tyr Val Gly Leu Arg Leu Ser Ser Leu Gln
    50                  55                  60

Ala Gly Thr Lys Glu Asp Leu Tyr Leu His Ser Leu Lys Leu Gly Tyr
65                  70                  75                  80

Gln Gln Cys Leu Leu Gly Ser Ala Phe Ser Glu Asp Asp Gly Asp Cys
                85                  90                  95

Gln Gly Lys Pro Ser Met Gly Gln Leu Ala Leu Tyr Leu Leu Ala Leu
            100                 105                 110

Arg Ala Asn Cys Glu Phe Val Arg Gly His Lys Gly Asp Arg Leu Val
        115                 120                 125

Ser Gln Leu Lys Trp Phe Leu Glu Asp Glu Lys Arg Ala Ile Gly His
    130                 135                 140

Asp His Lys Gly His Pro His Thr Ser Tyr Tyr Gln Tyr Gly Leu Gly
145                 150                 155                 160

Ile Leu Ala Leu Cys Leu His Gln Lys Arg Val His Asp Ser Val Val
                165                 170                 175

Asp Lys Leu Leu Tyr Ala Val Glu Pro Phe His Gln Gly His His Ser
            180                 185                 190

Val Asp Thr Ala Ala Met Ala Gly Leu Ala Phe Thr Cys Leu Lys Arg
        195                 200                 205

Ser Asn Phe Asn Pro Gly Arg Arg Gln Arg Ile Thr Met Ala Ile Arg
    210                 215                 220

Thr Val Arg Glu Glu Ile Leu Lys Ala Gln Thr Pro Glu Gly His Phe
225                 230                 235                 240

Gly Asn Val Tyr Ser Thr Pro Leu Ala Leu Gln Phe Leu Met Thr Ser
                245                 250                 255

Pro Met Pro Gly Ala Glu Leu Gly Thr Ala Cys Leu Lys Ala Arg Val
            260                 265                 270

Ala Leu Leu Ala Ser Leu Gln Asp Gly Ala Phe Gln Asn Ala Leu Met
        275                 280                 285

Ile Ser Gln Leu Leu Pro Val Leu Asn His Lys Thr Tyr Ile Asp Leu
    290                 295                 300

Ile Phe Pro Asp Cys Leu Ala Pro Arg Val Met Leu Glu Pro Ala Ala
305                 310                 315                 320

Glu Thr Ile Pro Gln Thr Gln Glu Ile Ile Ser Val Thr Leu Gln Val
                325                 330                 335

Leu Ser Leu Leu Pro Pro Tyr Arg Gln Ser Ile Ser Val Leu Ala Gly
            340                 345                 350

Ser Thr Val Glu Asp Val Leu Lys Lys Ala His Glu Leu Gly Gly Phe
        355                 360                 365
```

```
Thr Tyr Glu Thr Gln Ala Ser Ser Ser Gly Pro Tyr Leu Thr Ser Val
    370                 375                 380

Met Gly Lys Ala Ala Gly Glu Arg Glu Phe Trp Gln Leu Leu Arg Asp
385                 390                 395                 400

Pro Asn Thr Pro Leu Leu Gln Gly Ile Ala Asp Tyr Arg Pro Lys Asp
                405                 410                 415

Gly Glu Thr Ile Glu Leu Arg Leu Val Ser Trp
            420                 425

<210> SEQ ID NO 2
<211> LENGTH: 427
<212> TYPE: PRT
<213> ORGANISM: Homo sapiens

<400> SEQUENCE: 2

Met Arg His Leu Gly Ala Phe Leu Phe Leu Leu Gly Val Leu Gly Ala
1               5                   10                  15

Leu Thr Glu Met Cys Glu Ile Pro Glu Met Asp Ser His Leu Val Glu
                20                  25                  30

Lys Leu Gly Gln His Leu Leu Pro Trp Met Asp Arg Leu Ser Leu Glu
            35                  40                  45

His Leu Asn Pro Ser Ile Tyr Val Gly Leu Arg Leu Ser Ser Leu Gln
        50                  55                  60

Ala Gly Thr Lys Glu Asp Leu Tyr Leu His Ser Leu Lys Leu Gly Tyr
65                  70                  75                  80

Gln Gln Cys Leu Leu Gly Ser Ala Phe Ser Glu Asp Asp Gly Asp Cys
                85                  90                  95

Gln Gly Lys Pro Ser Met Gly Gln Leu Ala Leu Tyr Leu Leu Ala Leu
            100                 105                 110

Arg Ala Asn Cys Glu Phe Val Arg Gly His Lys Gly Asp Arg Leu Val
        115                 120                 125

Ser Gln Leu Lys Trp Phe Leu Glu Asp Glu Lys Arg Ala Ile Gly His
130                 135                 140

Asp His Lys Gly His Pro His Thr Ser Tyr Tyr Gln Tyr Gly Leu Gly
145                 150                 155                 160

Ile Leu Ala Leu Cys Leu His Gln Lys Arg Val His Asp Ser Val Val
                165                 170                 175

Asp Lys Leu Leu Tyr Ala Val Glu Pro Phe His Gln Gly His His Ser
            180                 185                 190

Val Asp Thr Ala Ala Met Ala Gly Leu Ala Phe Thr Cys Leu Lys Arg
        195                 200                 205

Ser Asn Phe Asn Pro Gly Arg Arg Gln Arg Ile Thr Met Ala Ile Arg
210                 215                 220

Thr Val Arg Glu Glu Ile Leu Lys Ala Gln Thr Pro Glu Gly His Phe
225                 230                 235                 240

Gly Asn Val Tyr Ser Thr Pro Leu Ala Leu Gln Phe Leu Met Thr Ser
                245                 250                 255

Pro Met Arg Gly Ala Glu Leu Gly Thr Ala Cys Leu Lys Ala Arg Val
            260                 265                 270

Ala Leu Leu Ala Ser Leu Gln Asp Gly Ala Phe Gln Asn Ala Leu Met
        275                 280                 285

Ile Ser Gln Leu Leu Pro Val Leu Asn His Lys Thr Tyr Ile Asp Leu
290                 295                 300

Ile Phe Pro Asp Cys Leu Ala Pro Arg Val Met Leu Glu Pro Ala Ala
305                 310                 315                 320
```

```
Glu Thr Ile Pro Gln Thr Gln Glu Ile Ile Ser Val Thr Leu Gln Val
            325                 330                 335

Leu Ser Leu Leu Pro Pro Tyr Arg Gln Ser Ile Ser Val Leu Ala Gly
            340                 345                 350

Ser Thr Val Glu Asp Val Leu Lys Lys Ala His Glu Leu Gly Gly Phe
            355                 360                 365

Thr Tyr Glu Thr Gln Ala Ser Ser Ser Gly Pro Tyr Leu Thr Ser Val
            370                 375                 380

Met Gly Lys Ala Ala Gly Glu Arg Glu Phe Trp Gln Leu Leu Arg Asp
385                 390                 395                 400

Pro Asn Thr Pro Leu Leu Gln Gly Ile Ala Asp Tyr Arg Pro Lys Asp
            405                 410                 415

Gly Glu Thr Ile Glu Leu Arg Leu Val Ser Trp
            420                 425

<210> SEQ ID NO 3
<211> LENGTH: 39
<212> TYPE: PRT
<213> ORGANISM: Artificial
<220> FEATURE:
<223> OTHER INFORMATION: First part of binding region I from human TC
<220> FEATURE:
<221> NAME/KEY: PEPTIDE
<222> LOCATION: (1)..(39)
<223> OTHER INFORMATION: First part of binding region I from human TC

<400> SEQUENCE: 3

Leu Pro Trp Met Asp Arg Leu Ser Leu Glu His Leu Asn Pro Ser Ile
1               5                   10                  15

Tyr Val Gly Leu Arg Leu Ser Ser Leu Gln Ala Gly Thr Lys Glu Asp
                20                  25                  30

Leu Tyr Leu His Ser Leu Lys
            35

<210> SEQ ID NO 4
<211> LENGTH: 5
<212> TYPE: PRT
<213> ORGANISM: Artificial
<220> FEATURE:
<223> OTHER INFORMATION: Second part of binding region I from human TC
<220> FEATURE:
<221> NAME/KEY: PEPTIDE
<222> LOCATION: (1)..(5)
<223> OTHER INFORMATION: Second part of binding region I from human TC

<400> SEQUENCE: 4

Thr Ala Cys Leu Lys
1               5

<210> SEQ ID NO 5
<211> LENGTH: 83
<212> TYPE: PRT
<213> ORGANISM: Artificial
<220> FEATURE:
<223> OTHER INFORMATION: Binding region II from human TC
<220> FEATURE:
<221> NAME/KEY: PEPTIDE
<222> LOCATION: (1)..(83)
<223> OTHER INFORMATION: Binding region II from human TC

<400> SEQUENCE: 5

Ile Leu Ala Leu Cys Leu His Gln Lys Arg Val His Asp Ser Val Val
1               5                   10                  15
```

```
Asp Lys Leu Leu Tyr Ala Val Glu Pro Phe His Gln Gly His His Ser
            20                  25                  30

Val Asp Thr Ala Ala Met Ala Gly Leu Ala Phe Thr Cys Leu Lys Arg
        35                  40                  45

Ser Asn Phe Asn Pro Gly Arg Arg Gln Arg Ile Thr Met Ala Ile Arg
    50                  55                  60

Thr Val Arg Glu Glu Ile Leu Lys Ala Gln Thr Pro Glu Gly His Phe
65                  70                  75                  80

Gly Asn Val

<210> SEQ ID NO 6
<211> LENGTH: 27
<212> TYPE: PRT
<213> ORGANISM: Artificial
<220> FEATURE:
<223> OTHER INFORMATION: Binding region III from human TC
<220> FEATURE:
<221> NAME/KEY: PEPTIDE
<222> LOCATION: (1)..(27)
<223> OTHER INFORMATION: Binding region III from human TC

<400> SEQUENCE: 6

Arg Val Ala Leu Leu Ala Ser Leu Gln Asp Gly Ala Phe Gln Asn Ala
1               5                   10                  15

Leu Met Ile Ser Gln Leu Leu Pro Val Leu Asn
            20                  25

<210> SEQ ID NO 7
<211> LENGTH: 26
<212> TYPE: PRT
<213> ORGANISM: Artificial
<220> FEATURE:
<223> OTHER INFORMATION: Preferred binding region II from human TC
<220> FEATURE:
<221> NAME/KEY: PEPTIDE
<222> LOCATION: (1)..(26)
<223> OTHER INFORMATION: Preferred binding region II from human TC

<400> SEQUENCE: 7

Arg Val Ala Leu Leu Ala Ser Leu Gln Asp Gly Ala Phe Gln Asn Ala
1               5                   10                  15

Leu Met Ile Ser Gln Leu Leu Pro Val Leu
            20                  25

<210> SEQ ID NO 8
<211> LENGTH: 10
<212> TYPE: PRT
<213> ORGANISM: Artificial
<220> FEATURE:
<223> OTHER INFORMATION: General mimotope 1
<220> FEATURE:
<221> NAME/KEY: PEPTIDE
<222> LOCATION: (1)..(10)
<223> OTHER INFORMATION: General Mimotope 1
<220> FEATURE:
<221> NAME/KEY: X
<222> LOCATION: (2)..(2)
<223> OTHER INFORMATION: X1 = F, G, L
<220> FEATURE:
<221> NAME/KEY: X
<222> LOCATION: (3)..(3)
<223> OTHER INFORMATION: X2 = F, L, R
<220> FEATURE:
<221> NAME/KEY: X
<222> LOCATION: (5)..(5)
<223> OTHER INFORMATION: X3 = L, P, Q
<220> FEATURE:
<221> NAME/KEY: X
```

```
<222> LOCATION: (8)..(8)
<223> OTHER INFORMATION: X4 =  M, Q, Y
<220> FEATURE:
<221> NAME/KEY: X
<222> LOCATION: (9)..(9)
<223> OTHER INFORMATION: X5 =  D, F
<220> FEATURE:
<221> NAME/KEY: X
<222> LOCATION: (10)..(10)
<223> OTHER INFORMATION: X6 =  M, R

<400> SEQUENCE: 8

Ser Xaa Xaa Tyr Xaa Trp Asp Xaa Xaa Xaa
1               5                   10

<210> SEQ ID NO 9
<211> LENGTH: 10
<212> TYPE: PRT
<213> ORGANISM: Artificial
<220> FEATURE:
<223> OTHER INFORMATION: General mimotope 2
<220> FEATURE:
<221> NAME/KEY: PEPTIDE
<222> LOCATION: (1)..(10)
<223> OTHER INFORMATION: Gneneral Mimotope 2

<400> SEQUENCE: 9

Ser Phe Phe Tyr Ser Leu Cys Tyr Cys Trp
1               5                   10

<210> SEQ ID NO 10
<211> LENGTH: 13
<212> TYPE: PRT
<213> ORGANISM: Artificial
<220> FEATURE:
<223> OTHER INFORMATION: Mimotope
<220> FEATURE:
<221> NAME/KEY: PEPTIDE
<222> LOCATION: (1)..(13)
<223> OTHER INFORMATION: Mimotope

<400> SEQUENCE: 10

Cys Ser Leu Phe Tyr Leu Trp Asp Gln Asp Arg Cys Ser
1               5                   10

<210> SEQ ID NO 11
<211> LENGTH: 13
<212> TYPE: PRT
<213> ORGANISM: Artificial
<220> FEATURE:
<223> OTHER INFORMATION: Mimotope
<220> FEATURE:
<221> NAME/KEY: PEPTIDE
<222> LOCATION: (1)..(13)
<223> OTHER INFORMATION: Mimotope

<400> SEQUENCE: 11

Cys Ser Phe Arg Tyr Leu Trp Asp Gln Asp Arg Cys Ser
1               5                   10

<210> SEQ ID NO 12
<211> LENGTH: 13
<212> TYPE: PRT
<213> ORGANISM: Artificial
<220> FEATURE:
<223> OTHER INFORMATION: Mimotope
<220> FEATURE:
<221> NAME/KEY: PEPTIDE
<222> LOCATION: (1)..(13)
<223> OTHER INFORMATION: Mimotope
```

<400> SEQUENCE: 12

Cys Ser Gly Leu Tyr Pro Trp Asp Met Phe Arg Cys Ser
1               5                   10

<210> SEQ ID NO 13
<211> LENGTH: 13
<212> TYPE: PRT
<213> ORGANISM: Artificial
<220> FEATURE:
<223> OTHER INFORMATION: Mimotope
<220> FEATURE:
<221> NAME/KEY: PEPTIDE
<222> LOCATION: (1)..(13)
<223> OTHER INFORMATION: Mimotope

<400> SEQUENCE: 13

Cys Ser Phe Arg Tyr Gln Trp Asp Met Phe Arg Cys Ser
1               5                   10

<210> SEQ ID NO 14
<211> LENGTH: 13
<212> TYPE: PRT
<213> ORGANISM: Artificial
<220> FEATURE:
<223> OTHER INFORMATION: Mimotope
<220> FEATURE:
<221> NAME/KEY: PEPTIDE
<222> LOCATION: (1)..(13)
<223> OTHER INFORMATION: Mimotope

<400> SEQUENCE: 14

Cys Ser Gly Leu Tyr Pro Trp Asp Tyr Phe Met Cys Ser
1               5                   10

<210> SEQ ID NO 15
<211> LENGTH: 13
<212> TYPE: PRT
<213> ORGANISM: Artificial
<220> FEATURE:
<223> OTHER INFORMATION: Mimotope
<220> FEATURE:
<221> NAME/KEY: PEPTIDE
<222> LOCATION: (1)..(13)
<223> OTHER INFORMATION: Mimotope

<400> SEQUENCE: 15

Cys Ser Phe Phe Tyr Ser Leu Cys Tyr Cys Trp Cys Ser
1               5                   10

<210> SEQ ID NO 16
<211> LENGTH: 738
<212> TYPE: DNA
<213> ORGANISM: Artificial
<220> FEATURE:
<223> OTHER INFORMATION: Single chain antibody construct TC2_ScFv
<220> FEATURE:
<221> NAME/KEY: misc_feature
<223> OTHER INFORMATION: Single chain antibody construct TC2_ScFv

<400> SEQUENCE: 16
caggtgcagc tgaaacagtc aggacctggc ctactgcagc cctcccagag cctgtccatc      60
acctgcacag tctctggttt ctcattaact tactatggtg tacactgggt tcgccagtct    120
ccagtaaagg gtctggagtg gctgggagtg atatggagtg gtggagacac agactatgat    180
acaactttca tatccagact gagcatcagc aaggacaatt ccaagggcca agttttcttt    240
aagatgacca gtctgcaaac tgatgacaca gccatatatt actgtgccag aggaaggacc    300

```
tatggtatcc actttgacta ctggggccaa ggcaccactc tcacagtctc ctcaggtgga    360
ggcggttcag gcggaggtgg atccggcggt ggcggatcgg acattgtgat gtcacagtct    420
ccatcctccc tggctgtgtc agtaggagag aaggtcacta tgagctgcaa atccagtcag    480
agtctgttca acagtagaac ccgaaagaac tacttggctt ggtaccagca gaaaccaggg    540
cagtctccta aagttctgat ctactgggca tccactaggg aatctggggt ccctgatcgc    600
ttcacaggca gtggatctgg gacagatttc actctcacca tcagcagtgt gcaggctgaa    660
gacctggcaa tttattactg caagcaattt tatgatctgt ggacgttcgg tggaggcacc    720
aagctggaaa tcaaacgg                                                   738
```

<210> SEQ ID NO 17
<211> LENGTH: 729
<212> TYPE: DNA
<213> ORGANISM: Artificial
<220> FEATURE:
<223> OTHER INFORMATION: Single chain antibody construct 3C4_ScFv
<220> FEATURE:
<221> NAME/KEY: misc_feature
<223> OTHER INFORMATION: Single chain antibody construct 3C4_ScFv

<400> SEQUENCE: 17

```
gaggtgcagc ttcaggagtc gggacctggc ctggtgaaac cttctcagtc tctgtccctc     60
atctgcactg tcactggcta ctcaatcacc agtgattatg cctggaactg gatccggcag    120
tttccaggaa acaaactgga gtggatgggc tacataagct acagtggttc cactagctac    180
aacccatctc tcaaaagtcg aatctctatc actcgagaca catccaagaa ccagttcttc    240
ctgcagttga attctgtgac tactgaggac acagccacat attactgtgc aagaccctat    300
tactacggta ttaggggggtt tgcttactgg ggccaaggga ctctggtcac tgtctctgca    360
ggtggaggcg gttcaggcgg aggtggatcc ggcggtggcg gatcggacat ccagatgact    420
cagtctccag cctccctatc tgcatctgtg ggagaaactg tcaccatcac atgtcgagca    480
agtgaaaata tttacagtta tttagcatgg tatcagcaga tacagggaaa atctcctcag    540
ctcctggtct ataattcaaa aaccttagca gaaggtgtgc catcaaggtt cagtggcagt    600
ggatcaggca cacagttttc tctgaagatc aacagcctgc agcctgaaga ttttgggagt    660
tattactgtc aacatcatta tgttactccg tacacgttcg gagggggggac caagctggaa    720
ataaaacgg                                                             729
```

<210> SEQ ID NO 18
<211> LENGTH: 246
<212> TYPE: PRT
<213> ORGANISM: Artificial
<220> FEATURE:
<223> OTHER INFORMATION: Single chain antibody construct TC2_ScFv
<220> FEATURE:
<221> NAME/KEY: PEPTIDE
<222> LOCATION: (1)..(246)
<223> OTHER INFORMATION: Single chain antibody construct TC2_ScFv

<400> SEQUENCE: 18

Gln Val Gln Leu Lys Gln Ser Gly Pro Gly Leu Leu Gln Pro Ser Gln
1               5                   10                  15

Ser Leu Ser Ile Thr Cys Thr Val Ser Gly Phe Ser Leu Thr Tyr Tyr
            20                  25                  30

Gly Val His Trp Val Arg Gln Ser Pro Val Lys Gly Leu Glu Trp Leu
        35                  40                  45

```
Gly Val Ile Trp Ser Gly Gly Asp Thr Asp Tyr Asp Thr Thr Phe Ile
 50                  55                  60

Ser Arg Leu Ser Ile Ser Lys Asp Asn Ser Lys Gly Gln Val Phe Phe
 65                  70                  75                  80

Lys Met Thr Ser Leu Gln Thr Asp Asp Thr Ala Ile Tyr Tyr Cys Ala
                 85                  90                  95

Arg Gly Arg Thr Tyr Gly Ile His Phe Asp Tyr Trp Gly Gln Gly Thr
                100                 105                 110

Thr Leu Thr Val Ser Ser Gly Gly Gly Ser Gly Gly Gly Gly Ser
                115                 120                 125

Gly Gly Gly Gly Ser Asp Ile Val Met Ser Gln Ser Pro Ser Ser Leu
130                 135                 140

Ala Val Ser Val Gly Glu Lys Val Thr Met Ser Cys Lys Ser Ser Gln
145                 150                 155                 160

Ser Leu Phe Asn Ser Arg Thr Arg Lys Asn Tyr Leu Ala Trp Tyr Gln
                165                 170                 175

Gln Lys Pro Gly Gln Ser Pro Lys Val Leu Ile Tyr Trp Ala Ser Thr
                180                 185                 190

Arg Glu Ser Gly Val Pro Asp Arg Phe Thr Gly Ser Gly Ser Gly Thr
195                 200                 205

Asp Phe Thr Leu Thr Ile Ser Ser Val Gln Ala Glu Asp Leu Ala Ile
210                 215                 220

Tyr Tyr Cys Lys Gln Phe Tyr Asp Leu Trp Thr Phe Gly Gly Gly Thr
225                 230                 235                 240

Lys Leu Glu Ile Lys Arg
                245

<210> SEQ ID NO 19
<211> LENGTH: 243
<212> TYPE: PRT
<213> ORGANISM: Artificial
<220> FEATURE:
<223> OTHER INFORMATION: Single chain antibody construct 3C4_ScFv
<220> FEATURE:
<221> NAME/KEY: PEPTIDE
<222> LOCATION: (1)..(243)
<223> OTHER INFORMATION: Single chain antibody construct 3C4_ScFv

<400> SEQUENCE: 19

Glu Val Gln Leu Gln Glu Ser Gly Pro Gly Leu Val Lys Pro Ser Gln
  1               5                  10                  15

Ser Leu Ser Leu Ile Cys Thr Val Thr Gly Tyr Ser Ile Thr Ser Asp
                 20                  25                  30

Tyr Ala Trp Asn Trp Ile Arg Gln Phe Pro Gly Asn Lys Leu Glu Trp
             35                  40                  45

Met Gly Tyr Ile Ser Tyr Ser Gly Ser Thr Ser Tyr Asn Pro Ser Leu
         50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Arg Pro Tyr Tyr Tyr Gly Ile Arg Gly Phe Ala Tyr Trp Gly Gln
                100                 105                 110

Gly Thr Leu Val Thr Val Ser Ala Gly Gly Gly Ser Gly Gly Gly Gly
            115                 120                 125

Gly Ser Gly Gly Gly Gly Ser Asp Ile Gln Met Thr Gln Ser Pro Ala
130                 135                 140
```

```
-continued

Ser Leu Ser Ala Ser Val Gly Glu Thr Val Thr Ile Thr Cys Arg Ala
145             150                 155                 160

Ser Glu Asn Ile Tyr Ser Tyr Leu Ala Trp Tyr Gln Gln Ile Gln Gly
            165                 170                 175

Lys Ser Pro Gln Leu Leu Val Tyr Asn Ser Lys Thr Leu Ala Glu Gly
            180                 185                 190

Val Pro Ser Arg Phe Ser Gly Ser Gly Ser Gly Thr Gln Phe Ser Leu
        195                 200                 205

Lys Ile Asn Ser Leu Gln Pro Glu Asp Phe Gly Ser Tyr Tyr Cys Gln
        210             215                 220

His His Tyr Val Thr Pro Tyr Thr Phe Gly Gly Gly Thr Lys Leu Glu
225             230                 235                 240

Ile Lys Arg
```

COBALAMIN ASSAY

CROSS-REFERENCE TO RELATED APPLICATIONS

This application is a divisional application of U.S. patent application Ser. No. 12/611,455, filed Nov. 3, 2009 now U.S. Pat. No. 8,647,831, which is a divisional of U.S. application Ser. No. 10/536,327, filed Dec. 19, 2005 now U.S. Pat. No. 7,632,648, which is a 371 U.S. National Stage filing of PCT/GB03/05167, filed on Nov. 26, 2003, and claims benefit to Great Britain Application No. 0227544.4, filed Nov. 26, 2002, Great Britain Application No. 0228674.8, filed Dec. 9, 2002 and Great Britain Application No. 0307727.8, filed Apr. 3, 2003, the entire contents of which are incorporated herein by reference.

The present invention relates to a method of assaying for holotranscobalamin (holoTC) in samples of biological, especially mammalian origin, and to specific binding partners (sbp's) for transcobalamin (TC) for use in such assays, as well as to their production.

HoloTC is the complex between cobalamin and its serum transport protein transcobalamin.

Cobalamin or vitamin $B_{12}$ is a water soluble vitamin which forms part of the vitamin B complex found in foods. The core molecule consists of a corrin ring of four pyrole units which surround a cobalt atom. Cobalamin is the only vitamin which cannot be synthesised by animals and must be absorbed from food in the gut. It is synthesised by micro-organisms, in particular by anaerobic bacteria and yeasts.

Cobalamin functions in vivo as a co-enzyme and cobalamin enzymes are known to catalyse three types of reaction: (i) intra-molecular rearrangements, for example, the formation of succinyl CoA from L-methylmalonyl CoA; (ii) methylations, for example, the formation of methionine by methylation of homocysteine; and (iii) reduction of ribonucleotides to deoxyribonucleotides in some micro-organisms. It is also thought that cobalamin deficiency may disturb cytokine and growth factor regulation (see Miller, Reviews 60: 142-144 (2002) and Scalabrino et al. J. Neuroimmunology 127:37-42 (2002)).

In the process of digestion, cobalamin released in food by cooking or by the acid environment of the stomach is bound by a salivary protein called haptocorrin, hereinafter referred to as HC (but which is also referred to in the art as R-binder or transcobalamins I and III collectively), to form a complex. Pancreatic enzymes digest the cobalamin-haptocorrin complex, holohaptocorrin (holoHC), in the ileum, liberating cobalamin which is then bound to a protein called intrinsic factor, which is secreted by the gastric mucosa, to form a further complex. The cobalamin-intrinsic factor complex binds to a specific receptor in the lining of the terminal ileum, whereupon it is dissociated by a releasing factor and the cobalamin is transported actively across the membrane of the ileum and is secreted into the blood stream bound to its transporter protein transcobalamin (TC).

It should be recognised that TC has in the past been referred to as transcobalamin II (TCII). TC, apoTC and holoTC are used herein to denote TCII, apo-TCII and holo-TCII respectively.

Cobalamin does not circulate in the blood in a free form in any appreciable amount. About 99% of the cobalamin is bound by one of HC, TC and albumin.

The protein responsible for transporting cobalamin to target tissues is TC. TC is a critical trace protein without which cobalamin cannot cross cell membranes. Despite this important metabolic function only about 6-25% of cobalamin in the serum is bound to TC and most is carried by HC. TC is a single chain polypeptide of 45 kDa found primarily in serum, seminal fluid and cerebro-spinal fluid. Cobalamin bound TC (holo-TC), attaches to specific receptors on cell membranes and, once bound, the holo-TC complex is taken into cells by pinocytosis.

TC is synthesised by the liver, vascular endothelium, enterocytes, macrophages and fibroblasts and circulates predominantly as apo-TC, i.e. lacking bound cobalamin. It has a short half life of approximately 90 minutes.

The amino acid sequence of human TC is believed to be as follows:

```
                                             (SEQ ID NO: 1)
MRHLGAFLFL  LGVLGALTEM  CEIPEMDSHL  VEKLGQHLLP

WMDRLSLEHL  NPSIYVGLRL  SSLQAGTKED  LYLHSLKLGY

QQCLLGSAFS  EDDGDCQGKP  SMGQLALYLL  ALRANCEFVR

GHKGDRLVSQ  LKWFLEDEKR  AIGHDHKGHP  HTSYYQYGLG

ILALCLHQKR  VHDSVVDKLL  YAVEPFHQGH  HSVDTAAMAG

LAFTCLKRSN  FNPGRRQRIT  MAIRTVREEI  LKAQTPEGHF

GNVYSTPLAL  QFLMTSPMPG  AELGTACLKA  RVALLASLQD

GAFQNALMIS  QLLPVLNHKT  YIDLIFPDCL  APRVMLEPAA

ETIPQTQEII  SVTLQVLSLL  PPYRQSISVL  AGSTVEDVLK

KAHELGGFTY  ETQASSSGPY  LTSVMGKAAG  EREFWQLLRD

PNTPLLQGIA  DYRPKDGETI  ELRLVSW
```

The first 18 amino acids, shown in italics, are a leader sequence not found in the mature protein circulating in the blood. In addition, there are a number of known polymorphisms, of which the substitution of arginine in place of proline at position 259 (shown in bold) (SEQ ID NO: 2) is the most common and is equally as abundant as the sequence shown. Other described polymorphisms are M198T, I219L, Q234R and S376L.

Since cobalamin must be absorbed from food, any conditions which result in impaired gastric function, for example, gastroenteritis or conditions resulting in gastric atrophy, or an inability to produce functional haptocorrin, intrinsic factor, releasing factor, TC or TC receptors, can result in impaired uptake of cobalamin and resultant deficiency.

Certain population sub-groups, for example the aged, pregnant women, patients with chronic or acute gastrointestinal disease, those suffering from certain autoimmune diseases, those with a family history of pernicious anaemia and AIDS sufferers, are particularly prone to cobalamin deficiency.

The clinical manifestations of cobalamin deficiency are varied and numerous but primarily involve anaemia, megaloblastic haematopoiesis and functional and structural disorders of the nervous system. Around 60% of individuals diagnosed as being deficient in cobalamin are anaemic, but in many neurological symptoms are the only clinical signs observed. Around 10% of patients exhibit psychiatric symptoms and around 40% exhibit both neurological and psychiatric symptoms.

Early diagnosis of cobalamin deficiency is crucial to ensure a good prognosis for patients, since some of the manifestations of cobalamin deficiency, particularly the neuropsychiatric effects, are irreversible if not detected and alleviated by cobalamin therapy quickly.

It is desirable therefore to accurately assess the cobalamin level of an individual in an expedient and efficient manner, with a view to establishing whether or not the individual may be suffering from cobalamin deficiency. Since it is TC that is responsible for transporting cobalamin into cells, the holoTC content of a body sample provides a better indicator of cobalamin deficiency than does the total cobalamin content.

Because holoTC is present in body fluids in such low concentrations, previous assay methods have generally not been entirely satisfactory. A patient with a serum holoTCII level at the lower end of the normal range typically has a serum holoTCII concentration of around $30 \times 10^{-12}$ M and conventional assays based upon physical absorption of TC onto a solid substrate, e.g. silica, have a lower limit of detection at around $40 \times 10^{-12}$ M. Such assays are therefore of relatively little value for assessment of holo-TCII deficiency (see Wickramasinghe et al., J Clin Path 49: 755-758 (1996)).

In WO 00/17659, it was proposed that specific binding partners (sbp's) for TCII or holo-TCII be used in an assay method for holo-TCII, thereby providing a holo-TCII assay method which could more readily be adapted to automation and the requirements of a high-throughput analytical laboratory.

The inventors have now discovered a particular epitope of holoTC for which sbp's can be generated which have excellent discrimination between apoTC and holoTC. Further, by creating a cyclic peptide "mimotope" mimic of that holoTC epitope, sbp's can be produced which allow an assay method for holoTCII which is highly susceptible to automation and use in high throughput assays.

For assay methods easily adaptable to the major automatic platforms, e.g. Centaur® (Bayer, Germany), Elecsys® (Roche) or Axsym® (Abbott), sbp's for holoTC are needed. However, no sbp's with the discrimination between apoTC and holoTC required for such assay formats have yet been described. Assay methods utilising TC-specific binding partners are suitable for automation but require extra steps to separate and measure the holoTC content making the methods more difficult to automate and reducing the number of commercial platforms which can successfully handle the assay.

There are only a few literature reports of polyclonal antibodies with affinities for human TC (see Morelli et al J Lab Clin Med 89: 645-652 (1976); vanKapel et al Biochem Biophys Acta 676: 307-13 (1981); Quadros et al J Biol Chem 261: 15455-60 (1986); and Nexo et al Clin Chem, 46:1643-9 (2000)) and even fewer literature reports of monoclonal antibodies with affinities for human TC (see Carmel et al., Proc Soc Exp Biol Med 188: 77-81 (1988) and McLean et al Blood 89:235-242 (1997)). None of these authors claims to have found binders which discriminate between apoTC and holoTC. Quadros (Biochem Biophys Res Comm 222: 149-154 (1996)), used antibodies which blocked the binding of cobalamin to apoTC to study the transport of cobalamin into cells.

In fact, it has not been entirely clear whether the differences in physicochemical properties between the apo-form and the holo-form of transcobalamin are sufficient to allow development of antibodies, or other sbp's, specific for only one of the forms. Indeed reports that the natural holoTC receptor also binds apoTC with high affinity (see Nexø et al., Biochem Biophys Acta 628:190-200 (1980)) and the fact that no holoTC specific antibodies have been reported suggested that in practice it may not be possible to produce such sbp's.

Sbp's (i.e. specific binding ligands) such as antibodies, have two particular properties which are of great significance to their suitability for use in assays such as those of the invention. These are their affinity and their specificity. Affinities for antibodies range from about $10^7$ to about $10^{11}$ M$^{-1}$ and other sbp's can show affinities in a similar range. High affinity antibodies ($>10^9$ M$^{-1}$) are generally preferred in the art for diagnostic assays because they allow the capture of analytes at low concentrations.

Whether a sbp of high affinity can be found for a particular analyte is intrinsically dependent upon the surface charge and topology of the analyte. If suitable motifs (epitopes) exist then antibody, peptide, DNA/RNA oligomer or organic chemical binders which correspond to this motif can be generated by standard methods. Thus, for example, once a high affinity antibody to a particular epitope has been identified, this indicates that sbp's of other types with affinity for this epitope can be found. The affinity depends upon the intrinsic nature of the epitope and upon the degree of correspondence between the epitope and the binding site of the sbp (sometimes referred to as the paratope).

The second significant property shown by sbp's is specificity. This is the ability of an sbp to recognise its binding partner to the exclusion of other molecules found in the sample being tested. This typically depends upon which epitope of a molecule is recognised by the sbp, how unique this epitope is to the analyte molecule, and how exactly the binding site of the sbp corresponds. Since a binding region having high correspondence to the charge and topology of the analyte is required both for high affinity and high specificity sbp's, sbp's with high specificity generally also have high affinity.

The method by which sbp's are identified typically relies on repeated rounds of screening under increasingly stringent conditions in order to identify sbp's with a very high affinity for their binding partner. This identifies extremely strongly binding sbp's and it is assumed that the strongest binding ligand will be the most specific and show the greatest discrimination.

In contrast to the usual technique, we selected for antibodies of poor affinity and examined these. Unexpectedly, by this method, antibodies have been identified which display good specificity for holoTC over apoTC. These antibodies can be used in holoTC assays and for the identification of "mimotope" mimics of the specific holoTC epitope, from which further holoTC specific ligands can be generated, including those with high affinity as well as high specificity. The antibodies and those generated from the mimotope may in turn be used to identify (experimentally or computationally) the epitope on holoTC which confers the specificity.

The primary antibody identified will be referred to herein as "3C4" and displays at least a 70-fold specificity for holoTC over apoTC. The "3C4" antibody is of relatively weak affinity ($Ka<10^7$ M$^d$).

In a first aspect, the present invention therefore provides a specific binding partner for holoTC having a specificity for holoTC over apoTC of at least 40-fold, preferably at least 50-fold, and most preferably at least 70-fold (for example 100-fold or greater).

The sbp preferably shows the above apo/holo discrimination in the case of both native apo/holoTC and recombinant apo/holoTC. Most preferably the specificity between human native apoTC and holoTC is at least as great as between recombinant apoTC and holoTC.

We have found that at least 7 epitopes exist on human TC and of these at least one (referred to herein as epitope 4) occurs in holoTC and not in apoTC. Further, epitope 4 has been found to be present only in the non-reduced (ie nondenatured) protein and not in the reduced (denatured) protein, which indicates that epitope 4 is a conformational or discontinuous epitope.

Conformational epitopes are antigenic regions consisting of residues which are widely spaced in the primary (linear) sequence of the protein but are brought together in close proximity when the protein folds. Such epitopes cannot be deduced, predicted or modelled from a knowledge of the amino-acid sequence of the protein because they have no correlation to this. Such an epitope exists only in the 3-dimensional conformation of the protein.

The composition and sequence of the amino acids comprising a conformation specific epitope can currently only be deduced from knowledge of the crystal structure of the protein. However, no crystal structure of human holoTC, or TC, or of any of the cobalamin transporting proteins from any species, has been determined. Only a preliminary report on the crystallization of human TC has been published, indicating human TC crystallizes as two independent molecules in an asymmetric unit poorly suited for X-ray diffraction analysis (see Garau et al, Acta Cryst. D57:1890-2 (2001)). It is thus not currently possible to determine the exact epitope of a conformation specific antibody to TC. These preliminary data further indicate that a true, high definition, crystal structure of human TC may be impossible to generate with current methods.

However, the present inventors have surprisingly identified certain amino acids and amino acid regions of the TC sequence which may provide the epitopic region of epitope 4 as described herein.

In a further aspect, therefore, the present invention provides a specific binding partner for holoTC which binds to at least one point in at least one of the regions I, II or III of human TC;
I) Leu 39 to Lys 77 and Thr 265 to Lys 269
II) Ile 161 to Val 243
III) Arg 271 to Asp 297 (or preferably Lys 296).

Preferably, the specific binding partner for holoTC will bind to each of regions I and II, each of regions II and III or each of regions I and III. Most preferably, the specific binding partner will bind to each of regions I II and III.

In the most common human TC sequence, regions I to III will have sequences:

```
                              (SEQ ID NOS: 3 and 4 respectively)
I LPWMDRLSLE HLNPSIYVGL RLSSLQAGTK EDLYLHSLK and
  TACLK (SEQ ID NO: 5)
II ILALCLHQKR VHDSVVDKLL YAVEPFHQGH HSVDTAAMAG
   LAFTCLKRSN FNPGRRQRIT MAIRTVREEI LKAQTPEGHF GNV (SEQ ID NO: 6)
III RVALLASLQD GAFQNALMIS QLLPVLN
```

The amino acid residues thought to be significant are highlighted in bold. More preferably, the regions I to III will have sequences:
In the most common human TC sequence, these regions will have sequences:

```
I LPWMDRLSLE HLNPSIYVGL RLSSLQAGTK EDLYLHSLK and
  TACLK

II ILALCLHQKR VHDSVVDKLL YAVEPFHQGH HSVDTAAMAG
   LAFTCLKRSN FNPGRRQRIT MAIRTVREEI LKAQTPEGHF GNV (SEQ ID NO: 7)
III RVALLASLQD GAFQNALMIS QLLPVL
```

The amino acid residues thought to be highly significant are highlighted in bold.

Where a binding partner or ligand is described herein as binding to a region of a protein such as TC, this indicates that there is at least one interaction between the binding partner and at least one amino acid in the region. It will be unusual for all amino acids in a region to contribute to ligand binding but, preferably, binding will indicate that the ligand and at least two amino acids in the region interact, more preferably, three, four, five or more amino acids in the region (e.g. 8 or 10) will interact with the ligand. Interactions may be measured, for example, by examining the structure of the ligand when crystallised or modelled with the protein. Distances of less than around 0.5 nm are typically considered to indicate interactions.

Preferred specific binding ligands for TC interact with the regions I to III by means of at least one of the significant residues highlighted above. More preferably, specific binding ligands for TC interact with the regions I to III by means of at least one of the highly significant residues indicated above. It is most preferred that at least half of the interactions are with the significant or highly significant residues indicated above.

In the absence of a crystal structure of human TC, mimotope mimics to epitope 4 of TC have been generated by use of the 3C4 antibody. A phage display library of disulfide constrained peptides was screened with the holoTC specific monoclonal antibody (mAb) 3C4 and a series of specific peptides were identified forming two similar motifs (see Example 4). The peptides were specific for mAb 3C4. They did not bind mAb directed to other epitopes on holoTC and binding to mAb 3C4 was blocked by holoTC, thus indicating that they were true mimics of, and competitors with, the holoTC specific epitope 4 (see Example) peptides, such as mimotopes, described herein are specified in terms of the standard biochemical single-letter codes for naturally occurring amino acids, which are all well known in the art. Of these, particularly significant to the present invention are; alanine (A), cysteine (C), aspartic acid (D), glutamic acid (E), phenylalanine glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y).

The mimotope provided consists of a constrained peptide with the motif

```
                                              (SEQ ID NO: 8)
          SX₁ X₂YX₃ WD X₄ X₅ X₆
where,    X₁ = F, G, L
          X₂ = F, L, R
          X₃ = L, P, Q
          X₄ = M, Q, Y
          X₅ = D, F
          X₆ = M, R
``` or the motif

```
                                              (SEQ ID NO: 9)
          SFFYSLCYCW
``` optionally attached to the surface of a cell or phage.

Such mimotopes and particularly polyhapten constructs thereof are useful in competition assays for holoTC, in which they may carry a suitable label. The mimotopes may also be used to identify alternative specific binding partners for holoTC having specificity for holoTC over apoTC and optionally having high affinity for holoTC.

The present invention therefore provides an assay method for holoTC comprising the use of a (preferably labeled) constrained peptide mimotope comprising the motif

```
                              (SEQ ID NO: 8)
              SX₁ X₂YX₃ WD X₄ X₅ X₆
where,        X₁ = F, G, L
              X₂ = F, L, R
              X₃ = L, P, Q
              X₄ = M, Q, Y
              X₅ = D, F
              X₆ = M, R or the motif (SEQ ID NO: 9)
              SFFYSLCYCW
``` optionally attached to a cell or phage, or a construct of two or more (e.g. 2, 3, 4, 5 or 6) such mimotopes. Such an assay method may be a method in which holoTC is pre-bound to a specific binding partner for holoTC and the remaining binding sites are detected by means of the mimotope. Preferably, however, the assay method is a competition assay in which the above described mimotope or construct thereof functions as a competitor of holoTC for specific binding sites on a specific binding ligand for holoTC.

In such an assay method, the sbp will generally be immobilised or immobilisable.

Typically, such an assay will involve contacting a sample from a human or animal subject with a limited quantity of a specific binding partner for holoTC having a restricted number of binding sites. HoloTC from the sample and the mimotope or mimotope construct then compete for binding to these sites. The bound and unbound portions are then preferably separated (e.g. by precipitation due to crosslinking or addition of a precipitation agent, rinsing of a substrate immobilized sbp, filtration, magnetic separation, centrifugation, change of conditions such as pH etc) to give a bound fraction and an unbound fraction. The holoTC in the sample may then be determined by measuring the amount of (optionally labelled) mimotope or mimotope polyhapten construct bound in the bound fraction or remaining unbound in the unbound fraction and relating this to the quantity of holoTC present in the sample. Greater amounts of mimotope binding to the sbp represent lesser amounts of holoTC in the sample. Where the bound or unbound mimotope or mimotope construct is capable of detection without separation of the bound and unbound fractions, e.g. by changes in light transmission following addition of an agglutination promoting agent or of fluorescence polarization where the holoTC sbp, the mimotope or construct is fluorophore-labelled, etc., the assay method need not involve separation of the bound and unbound fractions.

Suitable samples for the assessment of holoTC concentrations in all relevant aspects of the present invention may be any holoTC containing sample, e.g. a body fluid or tissue sample, or a sample prepared therefrom. Preferably, however the sample will be a body fluid, for example seminal fluid, cerebro-spinal fluid or amniotic fluid, more preferably a blood derived sample, particularly a serum sample.

Suitable specific binding partners in all aspects of the invention including assays for holoTC include antibodies, single chain antibodies, antibody fragments, antibody constructs, oligopeptides (e.g. constrained cyclic peptides), oligonucleotides (e.g. DNA or RNA aptamers), small organic molecules, etc., any of which may be immobilised or immobilisable. Preferred specific binding partners (e.g. for such assays) are antibodies, particularly monoclonal antibodies and their fragments and constructs (e.g. $F_{AB}$ fragments) and particularly preferred is monoclonal antibody 3C4 as described herein, its fragments and its constructs. Preferred sbps also include oligonucleotide aptamers (ie short, preferably constrained, sequences of double- or more usually single-stranded DNA or RNA). In certain cases these aptamers may be of value with a lower degree of specificity than is generally preferable. For example, they may show an at least 8-fold, preferably at least 10-fold and more preferably at least 15-fold specificity for holoTC over apoTC. Obviously it remains preferable that such aptamers have the higher specificity described above.

Particularly preferred sbps are single chain antibody fragments (scFv) comprising the heavy and light chain variable regions of the complete antibodies joined by a linker into a single polypeptide, coded for by a single DNA sequence. These may be prepared from the mRNA coding for the full antibodies by techniques known in the art. Such scFvs have the advantage that they are significantly smaller than complete antibodies and thus may be arrayed more closely and formed into constructs with a greater density of binding sites. They are also expressible in *E. Coli* and/or in bacteriophage and thus may be made in large quantities more easily than by expression in mammalian cell lines and are more amenable to genetic modification and optimisation. ScFvs are readily sequenced and the sequences of the scFvs corresponding to TC2 and 3C4 are given in Example 11 (Table 6). These scFvs were compared with the corresponding whole antibodies and found to have similar specificities (Example 11).

In addition to identifying scFvs with equivalent binding regions to TC2 and 3C4, the scFvs corresponding to 3C4 have been subjected to 2 rounds of affinity maturation by mutation and screening (see Example 13). Thus, where herein the use of antibody TC2 is indicated, it is similarly preferred that single chain antibody fragment ScFv_TC2, or an affinity matured equivalent, be used and where herein the use of antibody 3C4 is indicated, it is similarly preferred that single chain antibody fragment ScFv__3C4, or an affinity matured equivalent, be used.

The single chain antibody fragments may be labelled for detection by any of the methods described herein and where they are so labelled, it is preferred that the label be attached to the scFv via the linking region. Most preferably, the label will be attached to the linking region via a functional side chain, particularly the SH group of cysteine or the OH group of tyrosine.

The present invention thus further provides single chain antibodies corresponding to each of the antibodies described in the Examples herein and particularly to scFvs specific for epitopes 4 and 5 as described herein. Most preferable are TC2_ScFv and 3C4_ScFv as shown in Table 6 and the affinity matured equivalents indicated in Tables 9 and 10.

In order to improve the binding characteristics of 3c4_scFv, it was subjected to genetic modification and optimization (affinity maturation). Random mutagenesis libraries of size $10^5$-$10^6$ individual clones were generated and expressed on the surface of bacteriophage using techniques known in the art. The affinity maturation of scFv 3C4 resulted in 12 novel scFv clones with higher affinity and retained specificity for holoTC (Table 9). The best scFv clones were subjected to a second round of mutagenesis and library construction from which 9 novel scFv were selected, of which six with higher affinity than the best of the 1st generation library (clone 3.10E5 in Table 10). A method for performing affinity maturation by use of well-known techniques is described in Example 15.

Single-chain antibody fragments of monoclonal antibodies may be constructed, using standard procedures (e.g. McCafferty J, Hoogenboom H R, and Chiswell D J (ed.) (1996) *Antibody Engineering—A practical approach*, IRL Press, Oxford, UK). For convenience, commercially available kits may be used, such as the QuickPrp® mRNA Purification Kit, for mRNA preparation, the Mouse ScFv Module for scFv antibody preparation, and the Expression Module for expression of the scFv antibody as soluble protein in E. Coli (Amersham Biosciences). A typical method for the production of scFvs from any of the complete IgG antibodies described herein, by use of well-known techniques and commercially available kits is described in Example 12.

Specific binding partners suitable for an assay comprising use of the mimotopes described above will preferably be specific for an epitope overlapping with epitope 4 as described herein. Typically, such ligands will be specific for epitope 4.

Methods for the immobilisation of any of the ligands described herein are well known in the art and include covalent bonding such as by amide, disulphide or amine bond formation (e.g. by use of a carbodiimide coupling agent), physicochemical absorption such as absorption of thiols onto gold, coupling of immobilised specific binding partners (such as biotin and streptavidin or goat anti-mouse antibodies to capture murine mAbs) and the creation of insoluble antibody precipitates. Immobilised ligands may be pre-bound to a substrate or may be immobilised during an assay by the addition of a substrate or precipitation agent carrying a suitable binding partner.

Suitable substrates for immobilization of any of the specific binding ligands described herein are well known and include surfaces such as glass or polymeric surfaces, especially the surfaces of dishes or microtitre assay plates or sheets particularly the inside of the wells thereof, the surfaces of SPR slides, AFM slides etc., the surfaces of beads such as glass or polymeric beads, membranes, such as cellulose or polymeric membranes and also gels and macromolecules such as resins and dendrimers which swell or solubilise under certain conditions but may be precipitated or separated by techniques such as filtration or size exclusion chromatography. Most preferred as substrates are magnetisable polymeric beads such as those available from Bangs-Laboratories (e.g. Estapor® EMI-100/40), SPR chips (e.g. from Biacore) and the surfaces of microtitre plates.

Labelled species as described herein may be labelled for detection by any of a large number of methods known in the art. Such labelling methods include fluorescent labelling (e.g. with fluorosceine, rhodamine, green fluorescent protein etc.), luminescent labelling with proteins such as luciferase or with chemiluminescent agents (such as luminol (3-aminophthalphdrazide) or near-infrared luminescent metal azatriphenylene complexes), chromatic labelling with light absorbing or scattering agents such as dyes, enzymatic labelling (e.g. with alkaline peroxidase), radiolabelling with nuclei such as tritium, carbon-14, or radioiodine, with or without the use of scintillation agents, and magneto labelling, especially with paramagnetic substances such as ferrooxide labelled dextran. Scintillation proximity assays and fluorescence resonance energy transfer methods are also suitable. Magneto, luminescent and fluorescent methods, particularly chemiluminescent methods are preferred.

Where a detection method requires the addition of a cosubstrate, such as an oxidising agent, this will be added at a suitable stage, typically either simultaneously with the label or after suitable washing steps. Alternatively, species described herein may be "labelled" by means of their own mass. In such cases, these may be detected for example by Surface Plasmon Resonance (SPR), which technique is well known in the art and typically utilises SPR equipment from suppliers such as Biacore. Other physical methods of labelling include attachment to the "tip" of a force-microscope (e.g. an atomic force microscope (AFM) or chemical force microscope), whereby binding is detected by altered deflection of such a tip.

When used in any of the embodiments of the invention, the mimotopes and other peptides described herein may be synthetic peptides, formed by methods such as solid phase peptide synthesis, or may be formed by biosynthesis, such as by bacteria or by display on the surface of phage. Where the peptides (e.g. mimotopes) are biosynthesised, they may be secreted from the biosynthesising cell, phage, organism etc, or may be displayed on the surface thereof. In the case of surface display, the peptides will typically be displayed on phage, for example as a conjugate attached to all or a part of the phage coat protein. Such peptides (e.g. mimotopes or conjugates of epitopic regions) may be used in the methods of invention either by cleavage from the surface of the phage or by use of the whole phage, or that part or fraction of the phage which includes the displayed peptide. Where the peptide is to be used for generation of an immune response, the use of whole phage may have the advantage of provoking the immune system without the need to conjugate the peptide (mimotope etc.) to a separate immunogenic carrier.

In a further embodiment, the present invention provides a method for identifying specific binding partners for holoTC, having specificity for holoTC over apoTC of at least 40-fold, such as at least 50-fold, preferably at least 70-fold and most preferably 100-fold or more, comprising screening a library of potential specific binders with the above-described peptide mimotope, or constructs or conjugates thereof. Such a method will typically take the form of a "panning" assay, similar to that described using holoTC in Examples 1 and 2 below but has the advantage that the mimotope represents an epitope equivalent to epitope 4 of holoTC and therefore the majority of binders identified should possess specific binding for holoTC over apoTC. Suitable binders may comprise mAbs or fragments or constructs thereof, as described in Examples 1 and 2 below, but it will be clear that the same technique may be easily and routinely modified for the screening of other species, e.g. small organic molecules, aptamers, or oligopeptides (e.g. using peptide phage display libraries) in ways similar to those described in Example 4 below. Equally, such mimotopes and constructs thereof may be used in standard high throughput assay methods for identifying specific holoTC binders from synthetic peptide, oligonucleotide or small organic molecule libraries such as those commercially available.

Aptamers are a preferred type of sbp identifiable by screening against the above mimotopes. Where such DNA or RNA aptamers are identified they will preferably have the above specificity for holoTC over apoTC but remain of value when they have a specificity of at least 8-fold, preferably at least 10-fold and more preferably at least 15-fold.

In an additional embodiment, the present invention provides a method of inducing human-holoTC specific antibodies in a mammalian or preferably a non-mammalian (e.g. avian, piscine or reptilian) subject comprising administering the above-described mimotopes or immunogenic constructs and/or conjugates thereof (especially poly-hapten constructs thereof conjugated to suitable proteins, such as BSA) to said subject. Preferably said subject will be avian. Chickens are particularly suitable. The mimotope, construct or conjugate thereof will be immunogenic and will preferably present multiple copies of the mimotope for the purposes of inducing an immune response. Such a method will generally comprise administering a suitable antigenic construct of the above-describe mimotope, allowing a suitable period for an immune response to be generated, optionally administering one or more booster doses of the same or an alternative mimotope construct and extracting antibodies from the subject, either in the form of a polyclonal antibody extract, or preferably in the form of antibody-secreting cells, which may then be cultured using methods known in the art. In an embodiment of this method, human holoTCII or a fragment or construct thereof may be used for the initial immunisation of the non-mammalian subject, or for one or more of the booster immunisations, or both.

Specific binding partners for holoTC may also be identified by the use of peptide conjugates designed to express at least one of the epitopic regions I, II and III of epitope 4 described herein. Such peptides will be based upon the sequences from human holoTC;
I) Leu 39 to Lys 77 and Thr 265 to Lys 269
II) Ile 161 to Val 243
III) Arg 271 to Asp 297 (or preferably Lys 296).
Typically the regions will have the sequences indicated herein supra.

A suitable peptide conjugate will thus typically have sequence I, II or III, or fragments thereof, flanked by suitable linker sequences to provide a desirable, 3-dimensional presentation of the region. Preferably, all or parts of sequences I and II, sequences II and III or sequences I and III will be present with linker sequences between. More preferably, all three sequences I, II and III will be present, in whole or part, at least once in the conjugate (in any order) with linker sequences between and flanking sequences at one or both ends. All linker and/or flanking sequences may have cross-linkable points, such as cysteine residues, to allow control over the 3-dimensional structure of the peptide conjugate. The conjugates may also include mimotope sequences indicated above, either in addition to the regions I-III or in place of all or part of one or more of these regions. Suitable sequences may be synthesised chemically, or more typically will be expressed in cells or phage by methods analogous to those described herein for the expression of mimotopes.

Where parts of any of regions I to III are used herein, these parts are preferably include some of the significant or preferably highly significant residues indicated herein supra. Preferably at least half of these residues are present in equivalent positions in the conjugates to their positions in the sequences given supra.

The peptide conjugates described above form a further embodiment of the invention as does their use in assays and identifying specific binding partners for holoTC. The peptide conjugates (and their constructs, labelled equivalents etc.) may thus be substituted for the mimotopes described herein in any suitable embodiment of the invention including methods for identifying specific binders, assay methods and methods for inducing immune reactions.

In a yet further embodiment, the invention provides an assay method for assaying for holoTC in a sample (e.g. a liquid sample of biological origin), said method comprising contacting said sample with a specific binding partner for holoTC and detecting the resultant conjugates of holoTC and the specific binding partner, wherein said specific binding partner has a specificity for holoTC relative to apoTC of at least 40-fold, preferably at least 50-fold, more preferably at least 70-fold (see, e.g., Example 6 below).

In this method, as in conventional in diagnostic assays, detection of the conjugate may be direct or indirect and quantitative, semi-quantitative or qualitative. Direct detection may thus be of a property of the conjugate that differs from that of the unconjugated holoTC and sbp (e.g. mass or radiation emission, absorption or scattering characteristics). Indirect detection may for example be by detecting conjugates formed in competition to the holoTC:sbp conjugates or by detecting a conjugate of a further ligand (e.g. a labelled ligand) and the holoTC:sbp conjugate or by separation of the conjugate from the sample, release of cobalamin and detection of the released cobalamin. Qualitative and semi-quantitative detection may involve determining whether holoTC is present in the sample above or below a predetermined concentration limit or at higher or lower concentrations than in some selected standard, e.g. so as to provide a simple indication as to whether the source of the sample does or does not suffer from holoTC deficiency. Desirably the assay will involve quantitative determination of holoTC content, and optionally also total TC and/or total cobalamin content. The specific binding partner used in this assay method may also and preferably will be a specific binding partner for a constrained peptide comprising the motif (SEQ ID NO: 8)
$SX_1 \; X_2YX_3 \; WD \; X_4 \; X_5 \; X_6$ where,
$X_1$ = F, G, L
$X_2$ = F, L, R
$X_3$ = L, P, Q
$X_4$ = M, Q, Y
$X_5$ = D, F
$X_6$ = M, R or the motif (SEQ ID NO: 9)
SFFYSLCYCW and in particular may be a monoclonal antibody or fragment or construct or a DNA/RNA aptamer with such specificity. Furthermore, the holoTC sbp used in this method may, and preferably will, be blocked in binding to holoTC by the prior binding of certain other sbps with affinity for both apoTC and holoTC. In a preferred embodiment, the specific binding partner will be a monoclonal antibody with specificity for an epitope overlapping with epitope 4 of the TC as herein described or a fragment or construct of such an antibody. In particular, such an antibody will be specific for epitope 4 and, for example, may bind to any 1, any two or all three of regions I-II on TC, as described above. Most preferably such antibody, fragment or construct will be antibody 3C4 as herein described (or a corresponding scFv) or a fragment or construct thereof. Suitable specific binding partners may be identified by conventional techniques based on selection for binding to TC, to the mimotope or to an appropriate construct of regions I, II and/or III, as herein described.

The holoTC sbp selection process will typically involve (1) selecting for the ability to bind to holoTC and/or the mimotope or construct thereof and (ii) deselecting candidate sbp's without the required specificity with respect to holoTC and apoTC. Desirably the sbp selection process also involves deselection of candidate sbp's which bind to haptocorrin or other serum proteins as otherwise the holoTC assay of the invention will require TC to be separated from ETC or other blood proteins before being contacted with the sbp.

Accordingly, the holoTC sbp according to the invention is preferably an sbp which has a specificity for the said mimotope or construct, relative to apoTC of at least 40-fold, especially at least 50-fold, more preferably at least 70-fold. The holoTC sbp will also preferably have a selectivity for holoTC over the holo-forms of other cobalamin binding proteins (including, for example HC and intrinsic factor) of at least 50-fold, preferably at least 70-fold and more preferably 100-fold or more.

In the assay method of the invention, the holoTC specific binding partner may be used to capture holoTC, or may be used to identify holoTC previously captured by a secondary ligand.

Where the holoTC sbp is used to capture holoTC, it will generally be immobilised on a suitable substrate or immobilizable by use of an immobilising or precipitating agent as discussed above. Such substrates, agents and methods of immobilisation are well known in the art and include the methods described above. The holoTC captured by the holoTC specific binding partner may then be identified by contact with a secondary, optionally labelled ligand. Such a secondary ligand may be specific for holoTC but will generally be specific for TC (both apo- and holo-) and may bind to any epitope presented by the bound holoTC. Alternatively, the secondary ligand may be used to bind the captured holoTC and a labelled tertiary ligand with specificity for the secondary ligand. Such a tertiary ligand will then also be added, e.g. subsequently or simultaneously. Where detection is carried out by certain mass-sensitive or refractive index sensitive techniques such as SPR, the ligand may be "labelled" purely by its own mass.

A typical assay method utilising this "specific capture" technique comprises steps of:

contacting a liquid sample from a subject (such as a human patient or an animal, particularly a mammal) with an immobilised or immobilisable specific binding partner for holoTC to form a holoTC:sbp conjugate, contacting the specific binding partner with a secondary ligand for TC or holoTC such that the secondary ligand binds to the bound holoTC to form a holoTC:sbp:secondary ligand conjugate, separating the unbound secondary ligand from the holoTC:sbp:secondary ligand conjugate and optionally increasing the concentration of the holoTC:sbp:secondary ligand conjugate, optionally releasing the holoTC:sbp:secondary ligand conjugate from a substrate and/or a holoTC: secondary ligand conjugate from the sbp, wherein the release is preferably into a volume of liquid less than the volume of the liquid sample, optionally adding a cosubstrate or tertiary ligand to facilitate detection of the holoTC:sbp:secondary ligand conjugate or a holoTC:secondary ligand conjugate, detecting holoTC:sbp:secondary ligand conjugate or a holoTC:secondary ligand conjugate, and relating the detected amount of holoTC:sbp: secondary ligand conjugate or a holoTC:secondary ligand conjugate to the concentration of holoTC in the liquid sample to provide a quantitative, semi-quantitative or qualitative measurement of the holoTC present in the liquid sample, and optionally relating the holoTC present in the liquid sample to the presence or absence of cobalamin deficiency in the subject.

A preferred assay for holoTC described herein was constructed based on mAb 3C4 as the capture antibody and a non-overlapping, high-affinity antibody (Example 6.3) or aptamer (Example 14) as the detecting sbp. The accuracy of this assay was verified by comparison to a commercial assay for holoTC, HoloTC RIA® (Axis-Shield, Norway) (Example 7). The commercial assay is based on a different principle, namely solid-phase capture of total TC (apoTC holoTC) and release of cobalamin bound in holoTC followed by a competitive binding radioimmunoassay (Ulleland et al, Clin Chem 48:526-32 (2002)). The assay method of the invention correlated well with the commercial assay with r=0.96.

The binding of holoTC specific sbps such as 3C4 will be blocked by the prior binding of sbps specific for certain overlapping epitopes present on holoTC and optionally also present on apoTC. Examples of these blocking sbps include sbps specific for epitope 5 as described herein and particularly monoclonal antibody TC2 as described below. Additional examples are ligands which bind to at least one of regions I to III as described herein. Blocking of holoTC binding by these TC specific sbps may be used to further characterise the holoTC specific sbps of the present invention.

In a preferred assay method, forming a further aspect of the invention, an (optionally labelled) holoTC sbp is used as a detection ligand for holoTC previously, simultaneously or subsequently captured by an immobilised or immobilisable secondary ligand. Such secondary ligand may also be specific for holoTC, whereby to increase the specificity of the assay, but more preferably will bind both holoTC and apoTC. Preferably, such secondary ligand will have an affinity for TC which is greater than that of the holoTC sbp. Such an affinity may for example be at least $10^8 M^{-1}$, or at least $10^9 M^{-1}$ but is preferably at least $10^{19} M^{-1}$ and most preferably $10^{11} M^{-1}$ or greater. Especially preferably the TC capture ligand is one which does not cause a significant reduction in the specificity of the holoTC sbp for holoTC over apoTC. More preferably, the capture ligand should not cause a significant reduction in the affinity of the holoTC sbp for holoTC. Such preferred capture ligands include those which bind to an epitope which does not overlap with the epitope to which the holoTC sbp binds, and preferably does not bind in a way which causes any change in the conformation of the epitope to which the holoTC sbp binds. Preferred capture ligands are those which do not cause the specificity of the holoTC sbp to drop below at least 40-fold, preferably at least 50-fold, especially at least 70-fold. Generally preferred capture ligands will not bind to any of regions I to III as described herein.

A typical assay according to this embodiment of the invention may comprise the steps of:

contacting a known volume of liquid sample from an animal subject (particularly a mammal and preferably a human patient) with a capture ligand (such as an immobilised or immobilisable mAb, scFv or DNA/RNA aptamer) having specificity for TC, whereby to form a TC:capture ligand conjugate, optionally separating a fraction containing substantially all of the TC:capture ligand conjugate from a fraction containing substantially no TC:capture ligand conjugate, optionally in a known reduced volume, contacting said TC:capture ligand conjugate with a (preferably labelled) holoTC specific binding partner (such as a mAb, aptamer, specific binding peptide etc, as described above, particularly mAb 3C4 or a corresponding scFv) to provide a sbp:holoTC:capture ligand conjugate, optionally separating the unbound holoTC sbp from the sbp:holoTC:capture ligand conjugate, optionally adding a cosubstrate or tertiary ligand to facilitate detection of the bound holoTC sbp, detecting the bound holoTC, relating the detected bound holoTC sbp to the volumes to provide a quantitative, semi-quantitative or qualitative indication of the holoTC present in said liquid sample, and optionally relating the holoTC present in the liquid sample to the presence or absence of cobalamin deficiency in the subject.

The liquid sample may if desired be pretreated to increase the TC concentration therein and/or to remove or deplete HC (especially holoHC) and if desired albumin therein. This might typically involve application of a sample to a substrate to which HC or TC binds, separation of substrate and liquid phase and (where the substrate binds TC) release of TC from the substrate to form a new, preferably known lower volume, liquid sample. This HC depletion is particularly important when the final holoTC detection step involves detection of cobalamin released from the holoTC.

The steps of these methods may be appropriately re-ordered, in ways which will be obvious to those of skill in such assays, for example to allow the contact of the holoTC specific binder with the holoTC prior to the capture of the TC with the capture ligand.

Suitable capture ligands for use in the above assay method of the present invention bind one or more epitopes of TC other than the epitope (such as epitope 4 as herein described) bound by any holoTC specific binder. Further, the capture ligand should preferably bind to an epitope not overlapping with any such holoTC specific epitope. As described above, at least 7 epitopes of TC have been identified, of which at least 4 do not overlap with holoTC specific epitope 4. Preferably, and particularly when the liquid sample is contacted with the capture ligand prior to contact with any holoTC specific binder, the capture ligand should bind to an epitope or in such a fashion that the binding of any holoTC specific binder is neither inhibited nor made less holoTC specific.

The capture ligand should preferably bind in such a way that no substantial change is thereby made to the configuration of any holoTC specific epitope. These will generally not bind to any of regions I to III as described herein.

Monoclonal antibodies having no significant inhibitory effect on the binding or specificity of mAb 3C4 have been identified as described in the Examples below. Such antibodies are highly suitable for use as capture ligands in an assay method of the invention. In particular, ligands binding to epitope 2 as herein described are highly suitable for use as capture ligands in assay methods of the invention. Monoclonal antibody ligands to epitope 2 have been identified and are highly suitable. Most preferred capture ligands, however, are small ligands (such as scFvs), preferably with high affinity for TC. Small ligands may be bound more concentratedly a substrate and thus provide a greater concentration effect, allowing an increase in assay sensitivity. Antibody fragments, small peptide binders (particularly constrained peptides), nucleic acid oligomers (e.g. aptamers) and small organic molecules are all preferred small ligands. Fragments of mAbs (and scFvs) raised against epitope 2 are most preferred. Constructs comprising multiple repeats of such small ligands, which may be joined by chemical bonds and/or comparatively small linkers, are also suitable.

Where holoTC present in a liquid sample is captured by a TC specific capture ligand and contacted with a (preferably labelled) holoTC specific ligand for the purposes of detection of holoTC, the captured TC may (previously, simultaneously or preferably subsequently) be contacted with a TC detection ligand for the purposes of determining the total TC captured by the capture ligand and/or an apoTC detection ligand for the purposes of determining the apoTC captured by the capture ligand. The TC and/or apoTC content thereby determined may be related to the TC and/or apo TC content of the fluid sample, may be used to determine the holoTC saturation level of the TC, or may be used as an internal standard or verification by comparison with the determined quantity of holoTC.

Suitable TC detection ligands are preferably labelled specific binding partners for TC such as mAbs, aptamers, etc as described above which are specific for an epitope of TC not overlapping with either the epitope bound by the capture ligand (such as epitope 2 as described herein) or with the epitope bound by any holoTC specific binding ligand (e.g. epitope 4 as herein described). Suitable TC detection ligands also include the mAbs raised against epitopes 1, 3, 6 and 7 as described herein, and fragments and constructs thereof, optionally labelled in ways well known in the art and described above.

The labelling of any TC detection ligand may be the same or different from the labelling of any holoTC specific binder. Where methods such as SPR are used for detection, both labels will be detected by mass, usually sequentially. Where methods such as photometric detection (fluorescence, luminescence etc.) are used, the labels will preferably be distinguishable (e.g. by excitation and/or detection wavelength) and may be detected simultaneously or sequentially.

Suitable apoTC detection ligands may be ligands with specific binding affinity for apoTC over holoTC (e.g. cobalamin or cobalamin conjugates, optionally conjugated to a signal giving moiety) but are preferably ligands binding an epitope overlapping with the epitope bound by a holoTC specific binder (such as one of regions I to III). An assay utilising such a ligand will typically comprise the steps of binding captured TC from a liquid sample with a holoTC specific binder, subsequently contacting the captured TC with an apoTC detection ligand specific for an epitope present on both apoTC and holoTC but overlapping with the epitope bound by the holoTC specific binder and detecting the holoTC specific binder and the apo detection ligand. Such an apoTC detection ligand will be substantially prevented from binding to holoTC by the presence of pre-bound holoTC specific binder but will bind freely to the corresponding epitope on apoTC thereby providing a signal representing the amount of apoTC present in the fluid sample.

As with any TC detection ligand, the labelling of any apoTC detection ligand may be the same or different from the labelling of any holoTC specific binder. Where methods such as SPR are used for detection, both labels will be detected by mass, usually sequentially. Where methods such as photometric detection (fluorescence, luminescence etc.) are used, the labels will preferably be distinguishable (e.g. by excitation and/or detection wavelength) and may be detected simultaneously or sequentially. Preferably sequential detection will be used when the method used for detecting two ligands provides indistinguishable signals and simultaneous detection will be used when the signals from two ligands can be distinguished.

A further, highly preferred assay method of the invention utilizes mAb 3C4 as the detecting antibody (Examples 6 and 17). Such an approach has at least two advantages: (i) using as capture sbp (e.g. antibody) a mAb or aptamer with higher affinity for TC allows virtually all TC in a sample to be captured and concentrated; (ii) using mAb 3C4 as the detecting antibody increases the functional affinity of mAb 3C4. The KD for 3C4 was estimated at >100 nM, however, because monoclonal antibodies are divalent, making use of both binding sites decreases the off-rate and thus also decreases the functional KD (avidity). In the case of mAb 3C4, the off-rate was decreased from $2 \times 10^{-3}$ s$^{-1}$ to $2 \times 10^{-4}$ s$^{-1}$ when mAb 3C4 was used as detecting antibody rather than capturing antibody. As discussed above, a suitable capture antibody should preferably be a mAb that does not compromise the affinity or the specificity of mAb 3C4 for holoTC. We found that antibodies to epitope 2 best fulfilled these requirements. Although aptamer b974-3t1 as described herein overlapped partially with mAb 3C4 (see 11 and Example 17) this overlap was not sufficient to compromise the affinity or the specificity of mAb 3C4 and sufficient affinity was retained to fulfil the requirements of the assay (see Examples 16 and 17).

Simultaneous measurement of holoTC and apoTC in the same assay was also demonstrated utilizing antibodies directed to epitopes 4 and 5 (Examples 8 and 9). These epitopes overlap fully on holoTC while epitope 4 is not present on apoTC. Thus, by adding to a sample containing a mixture of apoTC and holoTC, first mAb 3C4, binding to epitope 4, and then mAb TC2, binding to epitope 5 and having the antibodies conjugated to different signal giving ligands, both apoTC and holoTC may be directly measured in the same sample. Alternatively, the apoTC and holoTC may first be captured and concentrated by a non-overlapping ligand (especially aptamer or monoclonal antibody), preferably of epitope 2 binding, prior to detection. Where apoTC is detected due to the "blocking" of one epitope present on apo-TC and holo-TC by binding to an epitope present only on holoTC (such as epitope 5 being blocked by binding to epitope 4), such blocking need not be complete. Providing the holoTC binding under certain conditions blocks a known proportion of the binding sites or that the number of sites revealed is insignificant in comparison to the total apoTC level then useful data can be generated. Preferably greater than 80% of the sites on holoTC will be blocked by the holoTC binding, more preferably 90% or more and most preferably at least 95%.

Further, simultaneous measurement of holoTC and total TC in the same assay was demonstrated utilizing antibodies directed to epitopes 4 and 6 (Example 10) and aptamer b974-3t1 (FIG. 12 Example 17). These epitopes do not overlap and neither one overlaps with epitope 2. Thus, by adding to a sample containing a mixture of apoTC and holoTC, first 3C4, binding to epitope 4, and then mAb 3C12, binding to epitope 6 and having the antibodies conjugated to different signal giving ligands, both apoTC and total TC may be directly measured in the same sample. Simultaneous measurement of holoTC and total TC in the same assay can also be accomplished by use of b974-3t1 as capture sbp and detecting holoTC and total TC using mAb 3C4 (epitope 4) and mAb 4-7 (epitope 2B) respectively (see Example 17).

In a further aspect the invention also provides a kit for use in an assay method according to the invention, said kit comprising an optionally labelled or immobilized specific binding partner for holoTC having a specificity for holoTC over apoTC of at least 40-fold (e.g. 50-fold or more); optionally and preferably an optionally labelled or immobilized TC binding ligand; optionally a plurality of holoTC solutions of known concentration; and optionally instructions for the performance of said assay method.

The present invention will be described further below by reference to the following non-limiting Examples and by reference to the accompanying drawings in which.

EXAMPLE 1

Figure 1A:
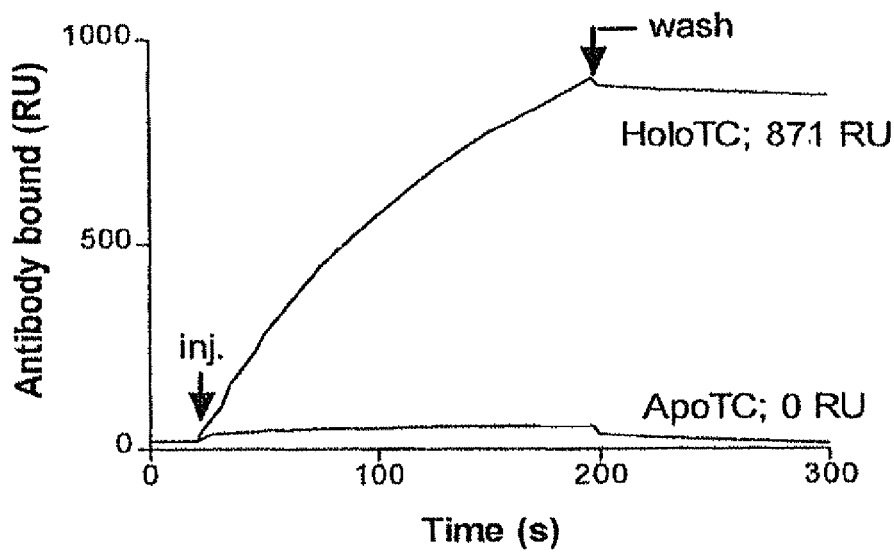
FIG. 1a represents the SPR "sensogram" showing the binding of mAb 3C4 to holoTC (871 RU) and absence of binding to apoTC (0 RU) immobilised to a chip by a mAb specific for epitope 2.

Development of Mouse Monoclonal Antibodies Specific for Human Transcobalamin and Human Holotranscobalamin 1.1) Immunization BALB/c female mice were injected i.p. with 20 µg of recombinant human holoTC mixed with AdjuPrime Immune modulator (Pierce, Ill., USA), followed by two booster injections of 20 µg at four week intervals.

1.2) Fusion

Four days after the final boost, spleens were removed and splenocytes fused to the HAT (Hypoxanthine, Aminopterin, Thymidine; Sigma) sensitive plasmacytoma OUR1 (a subclone of X63-Ag8.653) using PEG (Boehringer Mannheim, Germany). Fusion products were plated over 5×96F trays (Nunc) in the presence of HAT in culture medium (DMEMI-Ham's F12 (Invitrogen) plus 10% CPSR3 (Sigma). Fusions were fed after 1 week with culture medium containing HT (Sigma).

1.3) Primary Screening

After two weeks, medium from hybridomas was screened using a solid phase capture assay. The cell media were mixed with 10 µL of 1% (w/v) suspension of 1 µm magnetizable beads coated with a sheep anti-mouse IgG antibody (Merck-Estapor, France) and kept at ambient temperature for 1 h. The magnetizable beads with bound mouse monoclonal antibodies were isolated by using a magnet, and washed four times with 1 mL phosphate buffer, pH 7.2, 0.15 M NaCl and 1 mg/mL bovine serum albumin. Washed beads were resuspended in 100 µL of pooled human serum (Scantibodies, USA) which had been pretreated with 57Co-labelled cobalamin (ICN, USA) to convert apoTC in the serum into 57Co-labelled holoTC. The mixtures were kept at ambient temperature for 30 min and beads isolated by using a magnet. The radioactivity associated with the beads was counted in a gamma counter.

1.4) Cloning

Wells positive for anti-TC antibodies were cloned by limiting dilution over 96 wellF trays (Nunc), pre-seeded with Balb/c peritoneal feeder cells (10,000 per well). Positive clones were selected, and recloned until 100% of the sub-clones were producing specific antibody. Cell stocks were frozen in liquid nitrogen, in CPSR3 (Sigma) containing 10% DMSO (Sigma).

1.5) Secondary Screening

Antibodies from cell media were isolated on magnetizable beads as described above. Ten µL of the antibody coated beads were mixed with serum prelabelled with 57Co, as described above, in the presence of increasing concentrations of recombinant, human apoTC or holoTC.

Murine chimeric cell lines prepared as above and expressing the following antibodies were deposited at the European Collection of Cell Culture (ECACC), Porton Down, Salisbury, Wiltshire, SP4 (VG, UK in the name of Axis-Shield ASA:

| Antibody | Epitope | Accession No. | Date of deposit |
|---|---|---|---|
| 3C4 (3CY) | 4 | 02110741 | Nov. 7, 2002 |
| TC2 | 5 | 02110742 | Nov. 7, 2002 |
| 3C12 | 6 | 03090501 | Sep. 5, 2003 |
| TC7 | 2 | 03090502 | Sep. 5, 2003 |
| TC4 | 3 | 03090503 | Sep. 5, 2003 |
| 5H2 | 2 | 03090504 | Sep. 5, 2003 |

When used herein, the above epitope numbers are used as indicating the epitopes of TC and/or holoTC which are bound by the corresponding antibodies.

EXAMPLE 2

Affinities and Specificities of Selected Monoclonal Antibodies

The affinities and specificities of the monoclonal antibodies were evaluated by surface plasmon resonance using a Biacore instrument (Biacore, Sweden).

2.1) Immobilization of Rabbit Anti-Mouse IgG Polyclonal Antibody or Mouse Monoclonal Antibodies on Dextran Coated CM5 Chip The carboxylated surface of the a dextran coated CM5 chip (Biacore, Sweden) was activated according to protocol supplied by the manufacturer. In short 0.05M N-hydroxysuccinimide (NHS)/0.2 M N-ethyl-N'-[3-(dimethylamino)propyl] carbodiimide hydrochloride (EDC), was injected over the carboxylated chip at 10 pt/min for 7 min, then 50 µg/mL rabbit anti-mouse IgG polyclonal antibody in 10 mM acetate buffer, pH 5.0 is injected at 10 µL/min for 7 min, and finally the chip is blocked by injection of 1 M ethanolamine at 10 µL/min for 7 min. Immobilization of mouse monoclonal antibodies on the dextran coated chip was performed in the same way.

2.2) Binding of Mouse Monoclonal Antibodies to Rabbit Anti-Mouse IgG Coated Dextran Chip Mouse monoclonal antibodies which were not available in purified form and thus could not be directly immobilized on to the dextran coated chip (Example 2.1) were bound to the rabbit anti-mouse IgG coated dextran chip. Antibodies were diluted to circa 50 µg/mL in 0.01 M HEPES buffer, pH 7.4, 0.15 M, 0.003 M EDTA and 0.005% (v/v) Surfactant P20 (HBS-EP) and injected over the chip at 5 µL/min for 3 min. The binding of monoclonal antibody was followed in real time and the amount of mass bound was recorded in RU (Refractive units) in the sensorgram.

2.3) Binding of apoTC and holoTC to Mouse Monoclonal Antibodies

Figure 1B:
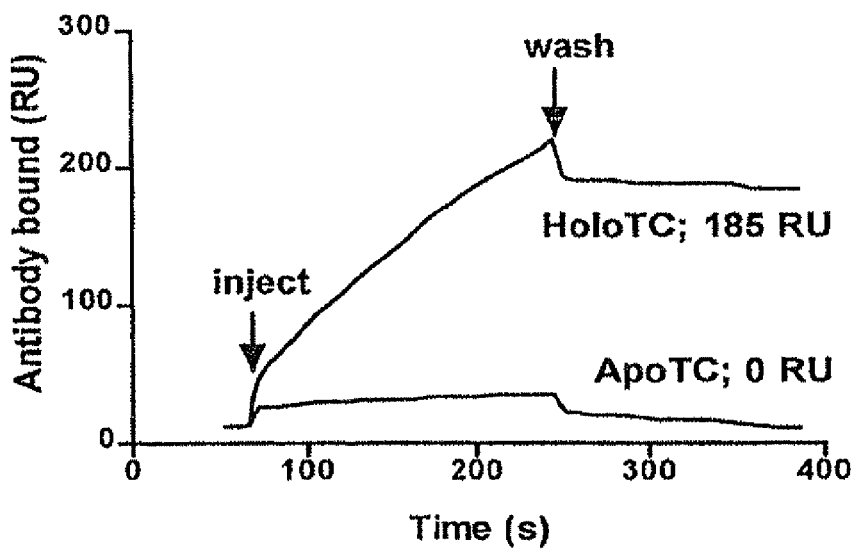
FIG. 1b is equivalent to FIG. 1 with mAb 5H2 (epitope 2) as capture ligand—the binding of mAb 3C4 to holoTC (185 RU) and absence of binding to apoTC (0 RU) are shown.

ApoTC and holoTC were diluted in HBS-EP to different concentrations and injected over the chip with immobilized mouse monoclonal antibody at 5 µL/min for 3 min. The on and off rates of binding were recorded for different concentrations of apoTC and holoTC and the affinity constants estimated (Table 1). Typical sensograms generated by this method is shown in FIGS. 1a and 1b.

2.4) Epitope Mapping

Figure 3A:
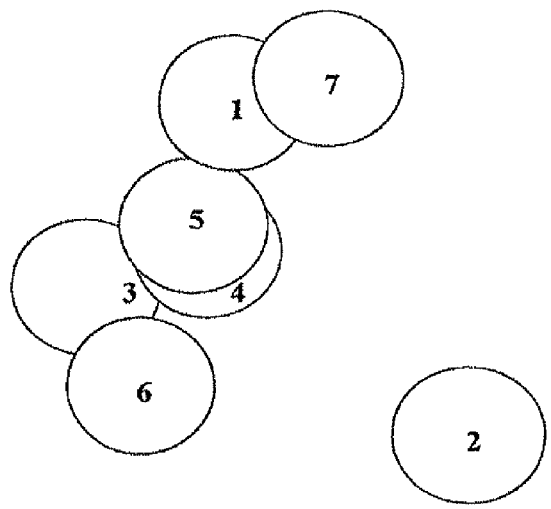
FIG. 3a represents an "epitope map" of TC as generated by the epitope mapping method described herein.
Figure 3B:
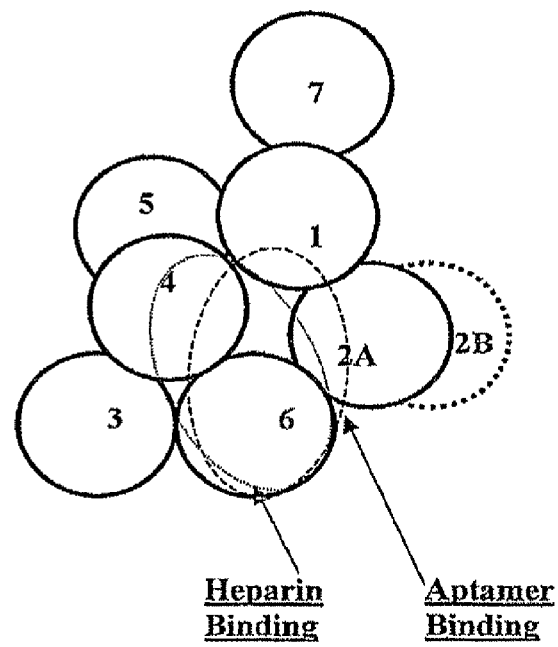
FIG. 3b represents a modified "epitope map" of TC as generated by the epitope mapping method described herein.
Figure 3C:
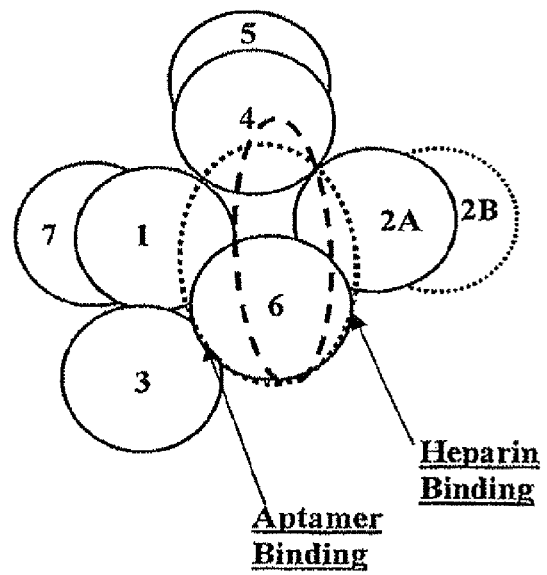
FIG. 3c represents a further modified "epitope map" of TC as generated by the epitope mapping method described herein.

The epitope specificity pattern was characterized with a panel of 17 mAb to create a functional epitope map (Table 1). Antibodies were bound pairwise to holoTC or apoTC. A first mAb was either immobilized onto the dextran coated chip as described in Example 2.1 or bound to the anti-mouse IgG chip. In the latter case, 1:10 diluted mouse serum was then injected in order to saturate excess binding sites on the anti-mouse IgG chip. HoloTC or apoTC was injected and bound to the first mAb followed by the second mAb. All mAb were combined in all possible permutations and mAb that could not bind concurrently or whose binding were compromised by the first antibody were considered fully and partially overlapping, respectively. Based on overlap data an epitope map was then constructed (FIG. 3a). This epitope map was then expanded to that shown in FIG. 3b on the basis of the results of Example 17 below. The epitope map was then further expanded to accommodate the epitopic regions described in Examples 18 and 19, as shown in FIG. 3C. Table 2 depicts data for antibodies binding to each type of epitope.

Monoclonal antibodies to epitopes 4 and 5 could be separated only by their differential binding to apoTC. Whereas the epitopes overlapped completely on holoTC, they were fully separated on apoTC because epitope 4 was not (or was only very weakly) present on apoTC.

TC is known to have a binding site for the endogenous polysaccharide heparin. The inhibitory effect of unfractionated heparin of mean molecular weight 12000 Da (Sigma) on the interation between holoTC and various mAbs was also tested. As indicated in FIG. 3b, the heparin binding site was found to overlap strongly with epitope 6, somewhat with epitope 4 and to a lesser degree with epitope 2A.

Further experiments using a purified preparation of the epitope 6 antibody, 3C12, indicated that this epitope partially overlaps with epitopes 1 and 2.

Blood samples from TC deficient patients having an intra exonic cryptic splice site in the TC gene giving rise to a 27 amino acid deletion (117-144) in the expressed TC, were kindly provided by Dr. Fares Namour. The mutated TC was recognized by mAb 3-9 but not by mAb 2-2, indicating that epitope 2 overlaps significantly with the sequence 117-144. The common TC polymorphism P259R did not compromise recognition by any of the antibodies.

TABLE 1

Epitope mapping of human TC

| Name of mAb#1 | KD of mAb#1 (nM) | mAb overlapping with mAb#1 |
|---|---|---|
| 1-9* | 5-10 | 5-18, TC4 |
| 1-12* | 5-10 | 2-6, 3-5, 3-9, Q2-13 |
| 2-2* | 0.08 | 3-11, 4-7, 5H2, TC7 |
| 2-6* | <1 | 1-12, 3-5, 3-9, Q2-13 |
| 3-5* | 1-5 | 1-12, 2-6, 3-9, Q2-13 |
| 3-9* | 0.04 | 1-12, 2-6, 3-5, Q2-13, (Q2-2) |
| 3-11* | 0.08 | 2-2, 4-7, 5H2, TC7 |
| 4-7* | 0.17 | 2-2, 3-11, 5H2, TC7 |
| 5-18* | 10-100 | 1-9, TC4, (3C4, 3C12, TC2) |
| Q2-2* | 5-10 | (3-9) |
| Q2-13* | 5-10 | 1-12, 2-6, 3-5, 3-9, (TC2) |
| 3C4 | >100 | TC2, (5-18) |
| 3C12 | 5-10 | (5-18) |
| 5H2 | >100 | 2-2, 3-11, 4-7, TC7 |
| TC2 | 1-5 | 3C4, (1-12, 5-18, Q2-13) |
| TC4 | 5-10 | 1-9, 5-18 |
| TC7 | 10-100 | 2-2, 3-11, 4-7, 5H2 |

*Antibody from State University of New York.
Antibodies in parenthesis were partially overlapping with mAb#1

TABLE 2

| mAb | Isotype | Epitope | $Kd^1$ (nM) | holo/apo Specificity (–fold) |
|---|---|---|---|---|
| 3-9* | IgG1 | 1 | 0.04 | 1 |
| 5H2 | IgG1 | $2A^2$ | >100 | 4 |
| TC7 | IgG2a | $2B^2$ | 10-100 | 1 |
| TC4 | IgG1 | 3 | 5-10 | 1 |
| 3C4 | IgG1 | 4 | >100 | $>70^3$ |
| TC2 | IgG1 | 5 | 1-5 | 1 |
| 3C12 | IgG1 | 6 | 5-10 | 1 |
| Q2-2* | n.d. | 7 | 5-10 | 1 |

*Antibody from State University of New York (Ulleland et al, Clin Chem 48:526-32;(2002)), included for comparison purposes.
[1]Kd values for holoTC.
[2]Epitope 2 may be subdivided into two subgroups, A and B, based on the results obtained with heparin (see above) and aptamer b974-3t1 (see Example 15 and Table 11).
[3]Because of the high Kd value for apoTC and traces (<1%) of holoTC in the apoTC preparation, it was not possible unambiguously to determine if the specificity was better than 70-fold.

EXAMPLE 3

Specificities of Monoclonal Antibodies in Serum 3.1) Immobilization of Monoclonal Antibodies on Goat Anti-Mouse IgG Coated Magnetic Particles Monoclonal antibodies diluted to circa 7 μg/mL in PBS, pH 7.4 containing 1 mg/mL BSA were mixed with 0.2% (w/v) rabbit anti-mouse IgG coated magnetic particles of diameter 0.8 μm (Merck Eurolab, France) for 1 h at ambient temperature. Beads were then isolated by using a magnet, washed three times with cold PBS and resuspended in PBS, containing 1 mg/mL BSA.

3.2) Binding of Native holoTC to Immobilized Monoclonal Antibodies

10 μL of monoclonal antibodies bound to magnetic beads (3.1) were mixed with 100 μL serum pretreated with 57Co-cobalamin (circa 50 fmol; ICN, USA) to convert all apoTC to 57Co-labelled holoTC and allowed to stand at ambient temperature for 1 h. Beads were then sedimented using a magnet, washed twice with cold PBA containing 1 mg/mL BSA and, after sedimentation by a magnet, counted in a gamma counter.

3.3) Binding of Native apoTC to Immobilized Monoclonal Antibodies

10 μL monoclonal antibodies bound to magnetic particles (3.1) were mixed with 100 μL serum and allowed to stand at ambient temperature for 1 h. Beads were then sedimented by using a magnet, and the supernatant saved. The beads were washed twice with cold PBA containing 1 mg/mL BSA, and, after sedimentation by a magnet, resuspended in 100 μL PBS containing 1 mg/mL BSA and 57Co-cobalamin (circa 50 fmol) and kept at ambient temperature for 1 h, after which the beads were sedimented by a magnet, washed twice with PBS containing 1 mg/mL BSA and counted in a gamma counter. To estimate the amount of apoTC remaining in the serum supernatants these were treated with 57 Co-cobalamin (circa 50 fmol) and then with 10 μL of magnetic beads coated with a high affinity anti-TC antibody, which has the capacity to bind virtually all TC in a serum sample (see Ulleland et al, Clin Chem 48:526-32; 2002). The beads were sedimented using a magnet and counted in a gamma counter.

3.4) Specificity of Monoclonal Antibodies for Native holoTC

Figure 2:
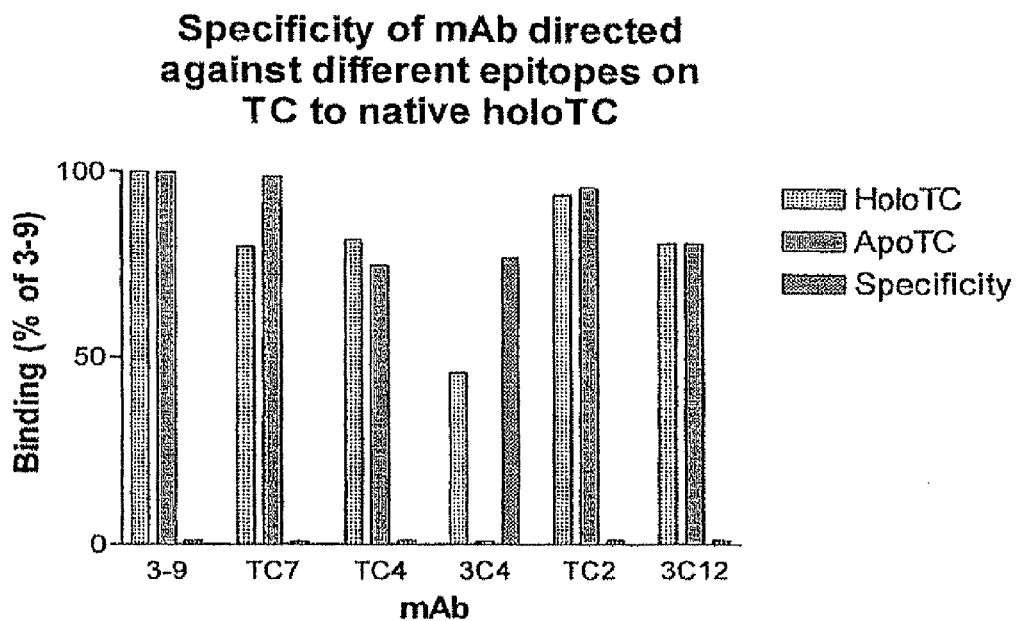
FIG. 2 represents the affinity and specificity of various antibodies described herein for native holoTC and apoTC.

The binding of holoTC and apoTC by the monoclonal antibodies were compared to that of a monoclonal anti-human TC antibody which had been previously determined to quantitatively remove holoTC and apoTC from serum (see Ulleland et al, Clin Chem 48:526-32; (2002)). The results are depicted in FIG. 2. The monoclonal antibody specific for epitope 4 (mAb 3C4) bound holoTC but no detectable amounts of apoTC. The antibodies to the other epitopes bound both holoTC and apoTC.

EXAMPLE 4

Biopanning of Phage Display Peptide Library with mAb 3C4

Disulfide cyclized 13 mer peptide libraries (Cosmix Molecular Biologicals GmbH, Germany) were panned; however, any peptide library of sufficient variability (>$10^8$ variants) and preferably constrained to decrease flexibility might be used.

4.1) Coupling Procedure for mAb 3C4

20 μL of Dynal® Carboxybeads were washed three times in 1 mL P135 containing 0.005% Tween 20 (PBST). Activation of the beads was carried out in 100 μL 0.5M EDC/0.1M NHS for 10 min at room temperature. 4 mg of mAb 3C4 was immobilized to the beads in 100 μL acetate buffer, pH 4.0 for 45 min at room temperature. Blocking was performed with 100 mM ethanolamine in PBS. After blocking the beads were washed three times in PBS.

4.2) Panning Procedure

About $10^{12}$ packaged phagemide of each library were incubated for 1 h with 20 μL 3C4-coated beads. As a control 20 μL carboxybeads without target was used. After incubation beads were washed with PBST. Elution of packaged phagemids was performed with Glycine-HCl, pH 2.2 (Gly) for 10 min immediately followed by neutralization, with Tris-HCl, pH 8.0 (Tris). Amplification and purification of bound phage particles were carried out according to standard protocols. Basically, 1 mL phage is transferred to 1 mL of log-phase E. Coli cells. Incubate for 30 min without shaking and then for 30 min with shaking at 37 C. Centrifuge at 1000 g for 10 min and resuspend in 1 mL 2TY-medium (16 g tryptone, 10 g yeast extract and 5 g NaCl per L, pH 7.0, sterilize) and plate bacteria on a large square plate containing 100 μg/mL ampicillin and 1% glucose. Incubate plates over night at 30 C. Next day add 10 mL 2TY and loosen cells from plates. Add 100-500 μL to 50 mL 2TY containing 100 ug/mL ampicillin, 1% glucose and grow at 37 C to an OD600 of about 0.5, which takes about 2 h. Add 10-fold excess of helper phage, e.g. M13 phage, and incubate 30 min at 37 C without shaking and then 30 min with shaking. Centrifuge 1000 g and resuspend cells in 50 mL 2TY containing 100 μg/mL ampicillin and 50 μg/mL kanamycin. Incubate over night at 30 C, spin at 2500 g for 15 min, and transfer supernates to fresh tubes and add ⅕ volume 20% PEF, 2.5 M NaCl, Incubate on ice for 1 h, centrifuge 2500 g for 15 min, resuspend pellet in 1 mL PBS, spin at 1200 g for 2 min to remove residual bacteria and transfer supernates to fresh tubes and use 100 μL for next round of selection. Quantitative enrichment was observed already after the second round of panning, and clones from the second and third rounds were sequenced. Several clones occurred more than once and in all seven different sequences were obtained, forming two motifs:

Motif 1: (SEQ ID NO: 20)

$CSX_1$ $X_2YX_3WDX_4X_5X_6CS$
Where CS is part of the framework, and
$X_1$ = F, G, L
$X_3$ = L, P, Q
$X_5$ = D, F
$X_2$ = F, L, R
$X_4$ = M, Q, Y
$X_6$ = M, R Motif 2: (SEQ ID NO: 21)

CSFFYSLCYCWCS 4.3) Screening ELISA

Microtitre plates were coated with 100 μL, 1 μg/mL mAb 3C4 or unrelated control antibody in PBS over night at 4 C. Remaining binding sites were blocked with 20 mg/mL bovine serum albumin (BSA) in PBS for 1 h. Some wells were only coated with BSA. Monoclonal packaged phagemids were added at a concentration of $10^{10}$ to $10^8$ cfu per well in PBS and incubated for 1 h. Preparations of packaged phagemids were centrifuged to remove aggregates. Wells were washed 6 times with PBS containing 0.1% Tween-20 and 3 times with PBS. For detection of bound phages 100 μL of horse-radish peroxidase (HRP) conjugated anti-M12 antibody (e.g. Pharmacia) diluted ⅕₀₀₀ in PBS was added to each well and incubated for 1 h at ambient temperature. ELISA plates were washed 5 times with PBS containing 0.1% Tween-20 and 3 times with PBS. The chromogenic substrate o-Phenyldiamine in citric acid, pH 4.0 supplemented with H202 was added and the color generating reaction was stopped after 2-5 min by addition of 2 M $H_2SO_4$. Results are shown in Table 3.

TABLE 3

| Phagemid | Seq ID No. | Sequence | Amount of phagemid | ELISA (absorbance units) | | |
|---|---|---|---|---|---|---|
| | | | | anti-TC mAb | Control mAb | BSA |
| CS1-2p | 10 | CSLFYLWDQD RCS | $10^{10}$ | 0.287 | 0.228 | 0.327 |
| | | | $10^9$ | 0.224 | 0.199 | 0.277 |
| | | | $10^8$ | 0.245 | 0.188 | 0.264 |
| CS1-6p | 11 | CSFRYLWDQD RCS | $10^{10}$ | 1.065 | 0.203 | 0.275 |
| | | | $10^9$ | 0.664 | 0.172 | 0.270 |
| | | | $10^8$ | 0.406 | 0.173 | 0.254 |
| CS1-9p | 12 | CSGLYPWDMF RCS | $10^{10}$ | 0.769 | 0.213 | 0.221 |
| | | | $10^9$ | 0.539 | 0.204 | 0.220 |
| | | | $10^8$ | 0.259 | 0.209 | 0.216 |
| CS1-11p | 13 | CSFRYQWDMF RCS | $10^{10}$ | 0.645 | 0.242 | 0.304 |
| | | | $10^9$ | 0.559 | 0.258 | 0.278 |
| | | | $10^8$ | 0.348 | 0.252 | 0.268 |
| CS1-29p | 14 | CSGLYPWDYF MCS | $10^{10}$ | 0.335 | 0.148 | 0.141 |
| | | | $10^9$ | 0.189 | 0.136 | 0.147 |
| | | | $10^8$ | 0.156 | 0.125 | 0.127 |

TABLE 3-continued

| Phagemid | Seq ID No. | Sequence | Amount of phagemid | ELISA (absorbance units) | | |
|---|---|---|---|---|---|---|
| | | | | anti-TC mAb | Control mAb | BSA |
| CS1-31p | 15 | *CSFFYSLCYCW CS* | $10^{10}$ | 0.298 | 0.125 | 0.112 |
| | | | $10^9$ | 0.165 | 0.118 | 0.114 |
| | | | $10^8$ | 0.152 | 0.116 | 0.109 |

The amino acids depicted in italics are conserved and part of the framework of the library.

EXAMPLE 5

Evaluation of Specificity of Selected Phages by Surface Plasmon Resonance

Antibodies were covalently immobilized on a dextran coated CM5 chip as described in Example 2. Phages were diluted 10-fold in HBS-EP and injected at 10 μL/min for 3 min. The amounts of phagemid bound was recorded in real time and expressed in response units (RU). To evaluate blocking by holoTC, 1 μM of holoTC was injected at 10 μL/min for 5 min prior to the injection of phagemids at 10 μL/min for 3 min. Inhibition was computed as the number of RU of phagemid bound to 3C4 with pretreatment with holoTC divided with the number of RU bound without pretreatment, times 100.

TABLE 4

Binding of phagmids to mAb 3C4 and blocking by 1 μM holoTC.

| Phagemid | Phage bound (RU*) | Block by holoTC (RU) | Inhibition (%) |
|---|---|---|---|
| CS1-2p | 4 | n.d.[1] | n.d. |
| CS1-6p | 24 | 3 | 88 |
| CS1-9p | 35 | 1 | 87 |
| CS1-11p | 32 | 0 | 100 |
| CS1-29p | 20 | 3 | 85 |
| CS1-31p | 42 | 5 | 88 |
| CS1-37p | 0 | n.d | n.d. |

*RU, response units . . .
[1] n.d., not done.

TABLE 5

Binding of phagemids to anti-TC antibodies having different epitopes on TC.

| | | Phagemid | | |
|---|---|---|---|---|
| mAb | epitope | CS1-6 (RU) | CS1-11 (RU) | CS1-31 (RU) |
| 3-9* | 1 | 0 | 0 | 0 |
| 5H2 | 2 | 0 | — | — |
| TC4 | 3 | 0 | — | — |
| 3C4 | 4 | 45 | 32 | 42 |
| TC2 | 5 | 1 | — | — |
| 3C12 | 6 | 0 | — | — |

*Antibody from State University of New York (Ulleland et al, Clin Chem 48:526-32; (2002)). Used for comparison purposes.

EXAMPLE 6

Assay for Direct Measurement of holoTC 6.1) Iodination of Monoclonal Antibody 3-9
mAb 3-9 was labelled with 125I using IODO-GEN precoated iodination tubes (Pierce, USA) and a protocol supplied by the manufacturer. In short, the tube containing 50 μg evaporated IODO-GEN® iodination reagent is rinsed with 1 mL 0.025M Tris, 0.4 M NaCl, pH 7.4 (Tris). Then 50 μg antibody in Tris is added and incubated for 5 min at ambient temperature. 50 μl, 10 mg/mL tyrosin in Tris is added and incubated 5 min and then the mixture is chromatographed on a column of NAP-5 equilibrated with 10 mL 0.01M phosphate buffer, 0.3 M NaCl, 0.01% merthiolate, and 1 mg/mL BSA, pH 7.3.

6.2) Immobilization of holoTC Specific mAb 3C4 on Magnetic Beads
4 mg Estapor® EMI-100/40, 0.83 μm magnetic beads were washed three times in 4 mL ice cold 0.05 M MES buffer, pH 6.0 (MES). Activation was carried out in 42 mL 0.063 M EDC/0.033 M sulfo-NHS for 15 min at ambient temperature. The activated beads were rinsed two times in 30 mL MES. 2.8 mg mAb 3C4 was immobilized on the beads in 6.8 mL MES for 2 h at ambient temperature. Blocking was performed with 5 mg/mL BSA, 0.05 M ethanolamine in PBS. After blocking beads were washed three times in PBS and resuspended in 40 mL PBS.

6.3) Assay for holoTC Using mAb 3C4 as Capture Antibody
800 μL of serum was mixed with 800 μL PBS and added 50 μl, of mAb 3C4 coated magnetic beads. After incubation at ambient temperature for 1 h, beads were separated by using a magnetic rack, washed three times with 400 μL PBS containing 1 mg/mL BSA (PBA), and resuspended in 400 μL PBA. Then, 50000 cpm of 125I-labelled mAb 3-9 was added and incubated for 1 h at ambient temperature. Beads were separated on the magnetic rack, washed three times with 400 μL PBA and counted in a gamma counter. The standard curve was constructed using calibrators made up of recombinant, human holoTC, and processed in parallel with the samples. A typical standard curve is seen in FIG. 4.

Figure 5A:
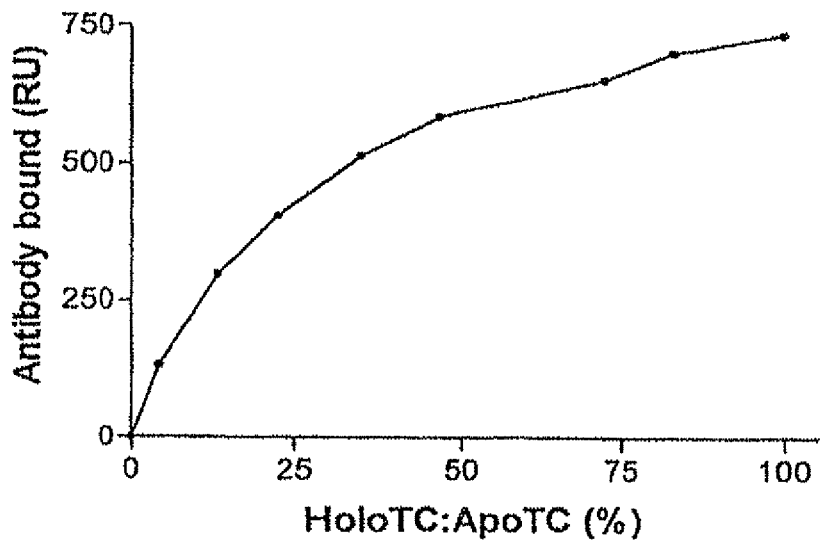
FIG. 5a represents a standard curve generated from standard mixtures of holoTC and apoTC in an assay method of the invention, showing the amount of mAb 3C4 as detection ligand bound to holoTC on a capturing antibody.
Figure 5B:
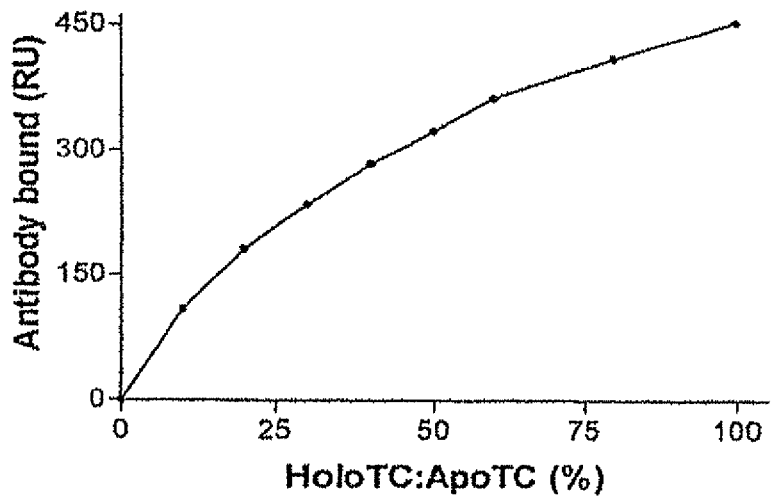
FIG. 5b is an equivalent curve to 5a showing the amount of mAb 3C4 as detection ligand bound to holoTC on a capturing antibody, wherein the capturing antibody is mAb TC7.

6.4) Assay for holoTC Using mAb 3C4 as Detecting Antibody
The binding events were followed in real time using surface plasmon resonance and performed on a Biacore instrument (Biacore™, Sweden). An anti-human TC monoclonal antibody directed against epitope 2 of TC was immobilized on a dextran coated CM5 chip, as described in Example 2.1, above. The chip with immobilized antibody was introduced into the instrument, after which was injected 15 μL of 18 ng/μL holoTC and apoTC. The proportion of holoTC to apoTC varied from 0:100 to 100:0, but the total amount was always the same, 18 ng/μL. Then 5 μL of 50 ng/μL mAb 3C4 was injected and the amount of antibody bound was recorded in the sensorgram. FIG. 5a depicts a typical standard curve. FIG. 5b depicts a curve generated in the same way wherein the cature ligand for epitope 2 was mAb TC7.

6.5) Conjugation of Monoclonal Antibody 3-11 with Horse-Radish Peroxidase
Mab 3-11 was conjugated to horse-radish peroxidase (HRP) using the EZ-Link™ Maleimide Activated HRP kit (Pierce, USA) and a protocol supplied by the manufacturer. In short, mAb 3-11 in PBS is modified with a 25-fold molar excess of SATA (N-succinimidyl S-acetylthioacetate) in DMF (dimethylformamide) and after 30 min deprotected with a 90-fold molar excess of hydroxylamine for 2 h at ambient temperature. The thiolated antibody is desalted and then allowed to react with an 8-fold excess of EZ-Link™ Maleimide Activated HRP at ambient temperature for 1 h. The conjugate is dialyzed three times against a 100-fold excess volume of PBS.

Figure 4A:
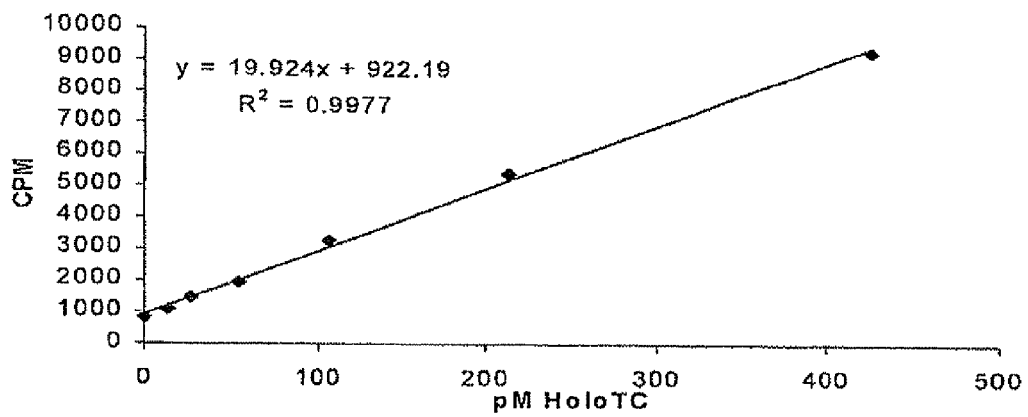
FIG. 4a represents the results of applying standard solutions of holoTC to an assay method for holoTC as described herein utilising antibody 3C4 as capturing antibody.
Figure 4B:
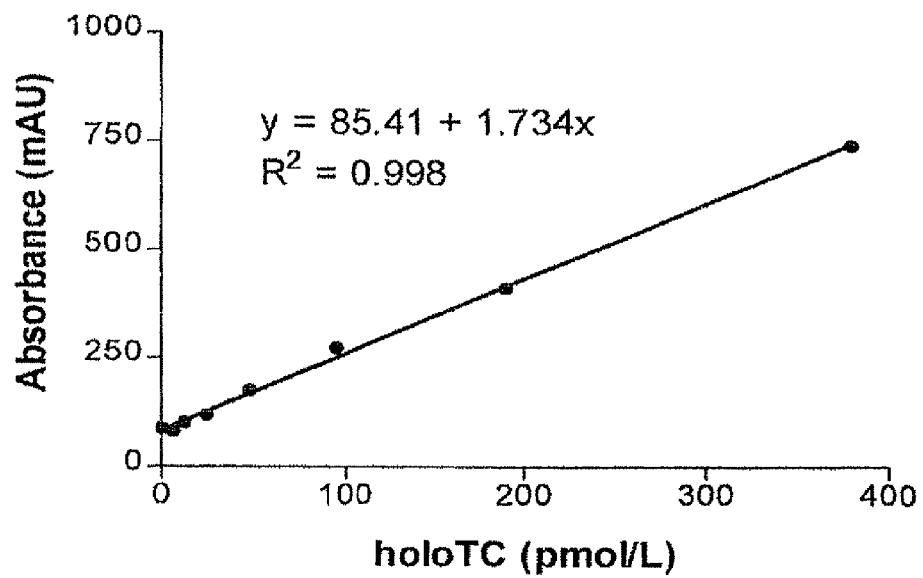
FIG. 4b represents the results of applying standard solutions of holoTC to an assay method for holoTC as described herein utilising antibody 3C4 as capturing antibody and using absorbance detection.

6.6) Conjugation of Antibody 3-11 with Alkaline Phosphatase mAb 3-11 was biotinylated using EZ-Link™ Sulfo-NHS-LC-Biotinylation kit (Pierce, USA) and a protocol supplied by the manufacturer. In short, 10 nmol of mAb 3-11 in PBS is mixed with 20-fold molar excess of Sulfo-NHS-LC-Biotin in deionized water. Kept on ice for 2 h and then purified protein on a gel filtration column equilibrated with PBS. Finally biotinylated antibody is allowed to bind streptavidin-conjugated alkaline phosphatase (Jackson ImmunoResearch Laboratories, Inc, USA), 6.7) Non-Isotopic Sandwich Assay for holoTC Using mAb 3C4 as Capture Antibody Maxisorb plates (NUNC-Immuno™, Denmark) were coated with 10 µg/mL mAb 3C4 in PBS over night at 4° C. and then blocked with 10 mg/mL BSA in PBS for 2 h at ambient temperature. To each well was added 50 µL of serum and 50 µL of PBS, and allowed to incubate for 30 min at ambient temperature. After washing three times with 200 µL of PBA+0.05% Tween (PBA+), 100 µL of HRP-conjugated mAb 3-11 (see 6.5) was added and the mixture left to incubate for 30 min at ambient temperature. Each well was washed three times with 200 µL PBA+ and 200 µL of the HRP-substrate, TMB (3,3',5,5'-tetramethylbenzidine; Kirkegaard & Perry Laboratories, USA) was added and incubated for 10 min. The reaction was quenched with 100 µL of 0.12M HCl and the color development measured at 450 nm. A typical standard curve is depicted in FIG. 4B.

6.8) Non-Isotopic Sandwich Assay for holoTC Using scFv 3C4 as Capture Antibody

Figure 4C:
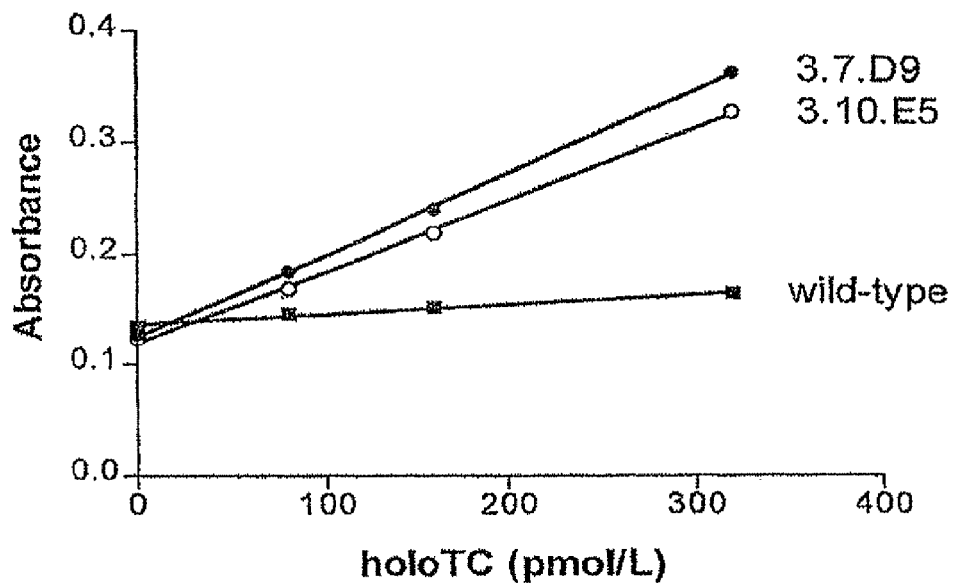
FIG. 4c represents the results of applying standard solutions of holoTC to assay methods for holoTC as described herein utilising holoTC specific single chain antibodies as capturing antibodies.

Maxisorb plates (NUNC-Immuno™, Denmark) were coated with 10 µg/mL anti-his-tag mAb (abeam, UK) in PBS over night at 4° C. and then blocked with 10 mg/mL BSA in PBS for 2 h at ambient temperature. To each well was added 50 µL of holoTC and 50 µL of PBS, and allowed to incubate for 30 min at ambient temperature. After washing three times with 200 µL of PBA+0.05% Tween (PBA+), 100 µL of HRP-conjugated mAb 3-11 (see 6.5) was added and the mixture left to incubate for 30 min at ambient temperature. Each well was washed three times with 200 µL PBA+ and 100 µL of the HRP-substrate, TMI3 (3,3',5,5'-tetramethylbenzidine; Kirkegaard & Perry Laboratories, USA) was added and incubated for 10 min. The reaction was quenched with 100 µL of 0.12M HCl and the color development measured at 450 nm. Typical standard curves using wt and two engineered mutants are depicted in FIG. 4C.

6.9) Non-Isotopic Bead Assay for holoTC Using mAb 3C4 as Capture Antibody

Figure 4D:
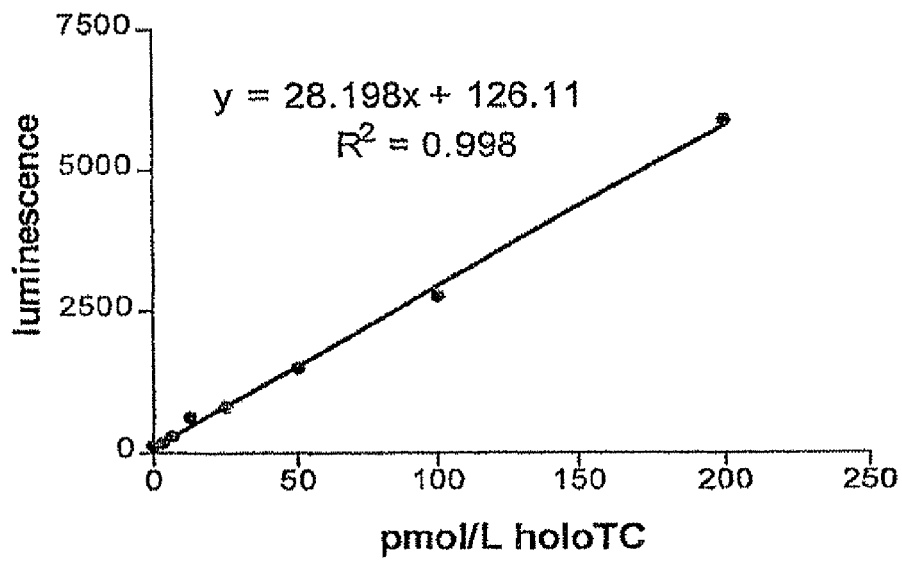
FIG. 4d represents the results of applying standard solutions of holoTC to an assay method for holoTC utilising antibody 3C4 as capturing antibody and using luminescence detection.

50 µL of serum and 50 µL of PBS were mixed with 10 µL of mAb 3C4 coated magnetic beads. After incubation at ambient temperature for 20 min, beads were separated by using a magnetic rack, washed six times with 200 µL pf PBA+, and resuspended in 100 µL of AP-conjugated mAb 3-11. After 20 min, beads were separated on the magnetic rack, washed six times with PBA+, added Lumiphos®Plus substrate (Aureon Biosystems GmbH, Austria), and read in a luminometer. A typical standard curve is seen in FIG. 4D.

EXAMPLE 7

Comparison Assay with Commercial Assay

Figure 6A:
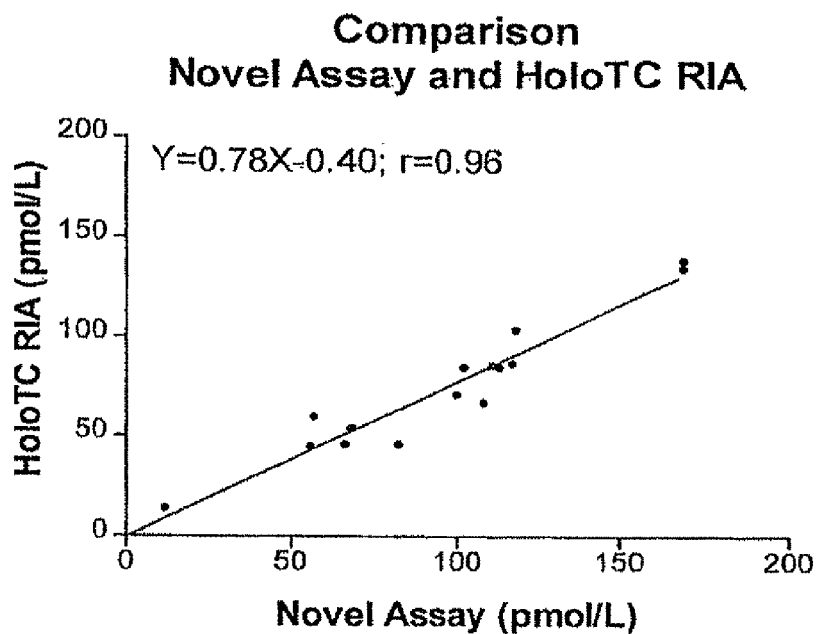
FIG. 6a represents a comparison between an assay method as described herein in and a commercial holoTC assay.
Figure 6B:
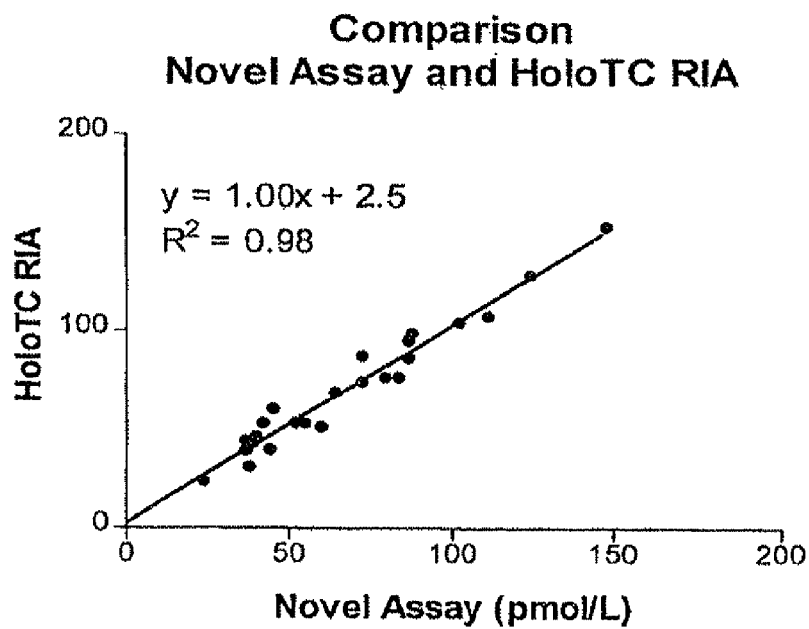
FIG. 6b represents a further comparison between an assay method as described herein in and a commercial holoTC assay.

Fifteen serum samples with holoTC values ranging from 14 µM to 139 µM as determined by a commercially available assay for holoTC, HoloTC RIA®, were quantified by the assay for holoTC described in Example 6.3. A comparison of the values obtained by the two methods showed a good correlation ($r=0.96$) (FIG. 6a).

Twenty four serum samples with holoTC values ranging from 24 µmol/L to 148 µmol/L as determined by a commercially available assay for holoTC, HoloTC RIAS, were quantified by the assay for holoTC described in Example 6.7. A comparison of the values obtained by the two methods showed a good correlation ($r=0.98$) (FIG. 68).

EXAMPLE 8

Dual Assay for holoTC and apoTC

Figure 7A:
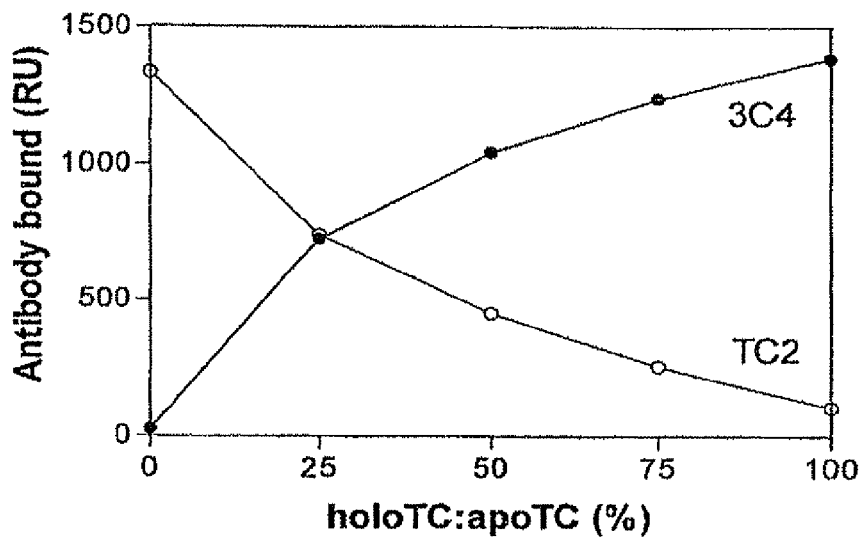
FIG. 7a represents the binding of antibodies specific for epitope 4 (3C4) and epitope 5 (TC2) sequentially to immobilised mixtures of holoTC and apoTC.
Figure 7B:
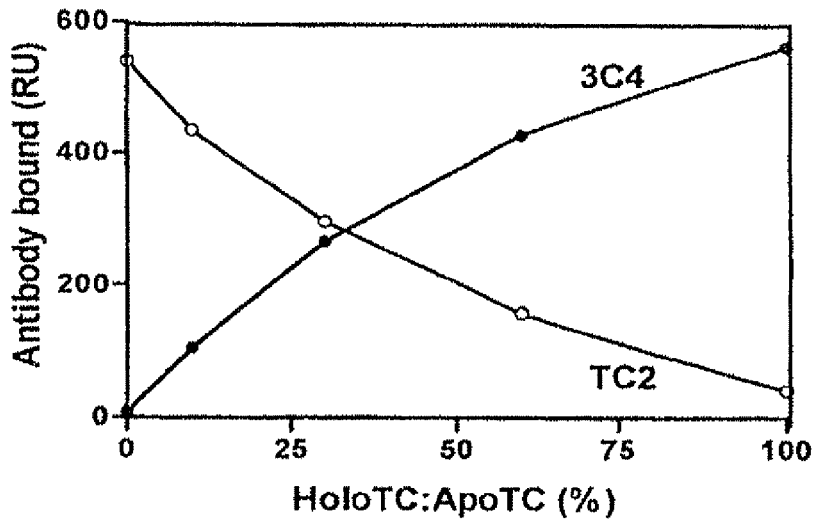
FIG. 7b represents the same binding as seen in FIG. 7a but the capture ligand is mAb TC7.

The binding events were followed in real time using surface plasmon resonance and performed on a Biacore instrument (Biacore™, Sweden). The capture antibody—a high affinity anti-human TC monoclonal antibody directed against epitope 2 of TC—was immobilized on a dextran coated CM5 chip, as described in Example 2.1, above. The chip with immobilized antibody was introduced into the instrument, after which was injected 15 µL of a mixture of holoTC and apoTC. The relative amounts of holoTC and apoTC varied but the total concentration of TC was constant, 18 ng/µL. The amount of holoTC bound was determined by injection of 60 µL of 400 ng/µL of the holoTC specific antibody, mAb 3C4. The amount of mAb 3C4 bound was recorded in the sensorgram. The chip was subjected to a wash step and then the amount of apoTC bound was determined by injection of 5 µL of 25 ng/µL of mAb TC2. mAb TC2 is specific for TC but overlaps completely with mAb 3C4 on holoTC, and thus when injected subsequent to mAb 3C4 detects only the apoTC fraction. FIGS. 7a and 7b depict the relation between apoTC and holoTC captured by the first antibody and the amount of mAbs 3C4 and TC2 bound. Because mAb 3C4 is a low affinity antibody complete blockage of holoTC is difficult to obtain, but because holoTC only makes up 6-25% of the total TC, >90% blockage is sufficient. In FIG. 7b, the first antibody is TC7.

EXAMPLE 9

Dual Assay for holoTC and apoTC

An anti-human TC specific monoclonal antibody, non-overlapping with epitopes 4 or 5, e.g. directed against epitope 2, is immobilized on magnetic beads as described in Example 2.1, above. An aliquot of serum or plasma (100-500 µL) is mixed with $1/10^{th}$ volume of the immobilized antibody and optionally with PBS (>100 µL) and allowed to incubate for 30 min at ambient temperature. The beads are sedimented using a magnet, washed twice with PBS and resuspended in PBS containing 1 mg/mL of BSA. An excess of mAb 3C4 conjugated to a signal giving moiety is added and incubated for 30 min, and the beads are then sedimented and washed as above, and resuspended in PBS containing 1 mg/mL of BSA. An excess of mAb TC2 conjugated to a different signal giving moiety is added and the mixture incubated for 30 min at ambient temperature. Beads are sedimented and washed as above. Finally, the bound mAb 3C4 and TC2 are measured using their respective signal giving moiety, and the holoTC and apoTC concentrations are determined by interpolation on a standard curve.

EXAMPLE 10

Dual Assay for holoTC and Total TC: TC Saturation

Figure 8:
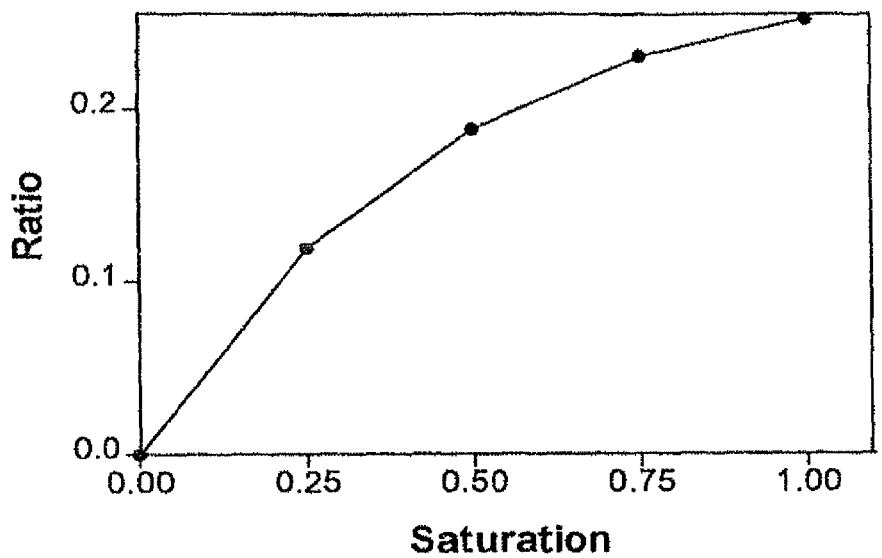
FIG. 8 represents a standard curve of TC cobalamin saturation showing the relative binding to epitopes 4 (by 3C4) and 6 (by 3C12) for holoTC and apoTC immobilised in known proportions.
Figure 9:
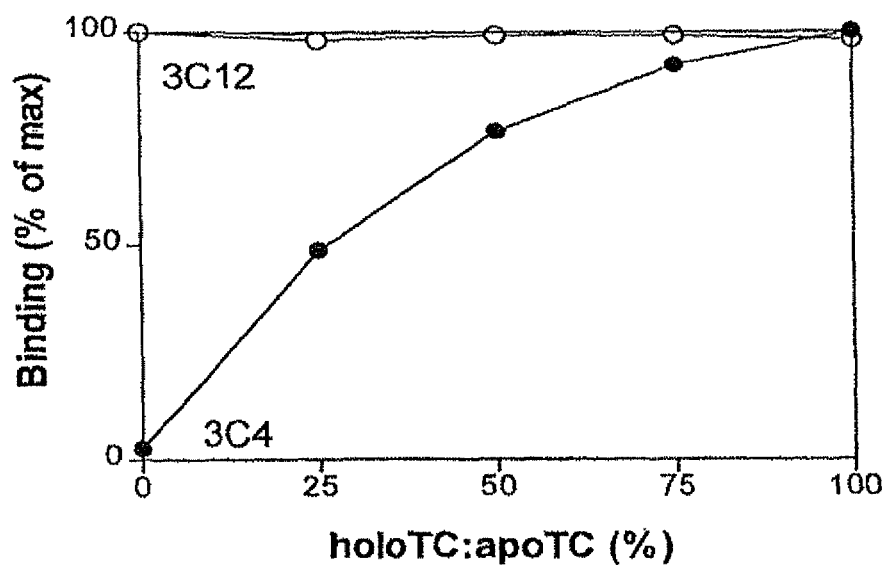
FIG. 9 represents the binding of antibodies specific for epitope 4 (3C4) and epitope 6 (3C12) sequentially to immobilised mixtures of holoTC and apoTC.

The binding events were followed in real time using surface plasmon resonance and performed on a Biacore instrument (Biacore™, Sweden). The capture antibody—a high affinity anti-human TC monoclonal antibody directed against epitope 2 of TC—was immobilized on a dextran coated CM5 chip, as described in Example 2.1, above. The chip with immobilized antibody was introduced into the instrument, after which was injected 15 μL of a mixture of holoTC and apoTC. The relative amounts of holoTC and apoTC varied but the total concentration of TC was constant, 18 ng/μL. The amount of holoTC bound was determined by injection of 60 μL of 400 ng/μL of the holoTC specific antibody, mAb 3C4. The amount of mAb 3C4 bound was recorded in the sensorgram. The chip was subjected to a wash step and then the total amount of TC bound was determined by injection of 15 μL of 100 ng/μL of mAb 3C12. mAb 3C12 is specific for TC and binds to epitope 6 which is non-overlapping with epitopes 2 and 4 (FIG. 3). By allowing mAbs 3C4 and 3C12 to bind the immobilized holoTC/apoTC, simultaneously or consecutively, the contents of both holoTC and total TC may thus be determined and expressed as absolute values or as the saturation level. FIG. 8 shows a typical standard curve for TC saturation. FIG. 9 depicts the binding of antibodies 3C4 and 3C12 to holoTC and total TC in the sample, respectively.

Table 6. Sequences of the single-chain Fv antibody fragments of monoclonal antibodies TC2 and 3C4.

VH sequences in capital letters followed by the linker sequence in lower case letters and finally VL sequences in capital letters:

EXAMPLE 11

Single Chain Antibody Fragments Corresponding to mAbs TC2 and 3C4

Single chain antibodies corresponding to TC2 and 3C4 were generated and sequenced. The sequences are shown in Table 6 wherein for each scFv the heavy chain variable region (VH) is shown in capitals, followed by the linker sequence in lower case, followed by the light chain variable region (VL) sequence. The scFVs having the sequences shown in Table 6 were immobilised on SPR chips and the binding kinetics compared with those of the corresponding whole IgG antibodies using the method described in Example 2. The results are shown in Table 7 which demonstrates that the specificity of the scFvs was equivalent to that of the corresponding whole antibodies.

TABLE 6

Sequences of scFvs

TC2_ScFv
(SEQ ID NO: 16)
CAGGTGCAGCTGAAACAGTCAGGACCTGGCCTACTGCAGCCCTCCCAGAG

CCTGTCCATCACCTGCACAGTCTCTGGTTTCTCATTAACTTACTATGGTG

TACACTGGGTTCGCCAGTCTCCAGTAAAGGGTCTGGAGTGGCTGGGAGTG

ATATGGAGTGGTGGAGACACAGACTATGATACAACTTTCATATCCAGACT

GAGCATCAGCAAGGACAATTCCAAGGGCCAAGTTTTCTTTAAGATGACCA

GTCTGCAAACTGATGACACAGCCATATATTACTGTGCCAGAGGAAGGACC

TATGGTATCCACTTTGACTACTGGGGCCAAGGCACCACTCTCACAGTCTC

CTCAggtggaggcggttcaggcggaggtggatccggcggtggcggatcgG

ACATTGTGATGTCACAGTCTCCATCCTCCCTGGCTGTGTCAGTAGGAGAG

AAGGTCACTATGAGCTGCAAATCCAGTCAGAGTCTGTTCAACAGTAGAAC

CCGAAAGAACTACTTGGCTTGGTACCAGCAGAAACCAGGGCAGTCTCCTA

AAGTTCTGATCTACTGGGCATCCACTAGGGAATCTGGGGTCCCTGATCGC

TTCACAGGCAGTGGATCTGGGACAGATTTCACTCTCACCATCAGCAGTGT

GCAGGCTGAAGACCTGGCAATTTATTACTGCAAGCAATTTTATGATCTGT

GGACGTTCGGTGGAGGCACCAAGCTGGAAATCAAACGG

3C4_ScFv
(SEQ ID NO: 17)
GAGGTGCAGCTTCAGGAGTCGGGACCTGGCCTGGTGAAACCTTCTCAGTC

TCTGTCCCTCATCTGCACTGTCACTGGCTACTCAATCACCAGTGATTATG

CCTGGAACTGGATCCGGCAGTTTCCAGGAAACAAACTGGAGTGGATGGGC

TACATAAGCTACAGTGGTTCCACTAGCTACAACCCATCTCTCAAAAGTCG

AATCTCTATCACTCGAGACACATCCAAGAACCAGTTCTTCCTGCAGTTGA

ATTCTGTGACTACTGAGGACACAGCCACATATTACTGTGCAAGACCCTAT

TACTACGGTATTAGGGGGTTTGCTTACTGGGGCCAAGGGACTCTGGTCAC

TGTCTCTGCAggtggaggcggttcaggcggaggtggatccggcggtggcg gatcgGACATCCAGATGACTCAGTCTCCAGCCTCCCTATCTGCATCTGTG

GGAGAAACTGTCACCATCACATGTCGAGCAAGTGAAAATATTTACAGTTA

TTTAGCATGGTATCAGCAGATACAGGGAAAATCTCCTCAGCTCCTGGTCT

ATAATTCAAAAACCTTAGCAGAAGGTGTGCCATCAAGGTTCAGTGGCAGT

GGATCAGGCACACAGTTTTCTCTGAAGATCAACAGCCTGCAGCCTGAAGA

TTTTGGAGTTATTACTGTCAACATCATTATGTTACTCCGTACACGTTCG

GAGGGGGGACCAAGCTGGAAATAAAACGG

TABLE 7

Amino acid sequences of scFvs

TC2_ScFv
(SEQ ID NO: 18)
QVQLKQSGPG LLQPSQSLSI TCTVSGFSLT YYGVHWVRQS

PVKGLEWLGV IWSGGDTDYD TTFISRLSIS KDNSKGQVFF

KMTSLQTDDT AIYYCARGRT YGIHFDYWGQ GTTLTVSSGG

TABLE 7-continued

Amino acid sequences of scFvs

```
GGSGGGGSGG GGSDIVMSQS PSSLAVSVGE KVTMSCKSSQ

SLFNSRTRKN YLAWYQQKPG QSPKVLIYWA STRESGVPDR

FTGSGSGTDF TLTISSVQAE DLAIYYCKQF YDLWTFGGGT

KLEIKR

3C4_ScFv
                                         (SEQ ID NO: 19)
EVQLQESGPG LVKPSQSLSL ICTVTGYSIT SDYAWNWIRQ

FPGNKLEWMG YISYSGSTSY NPSLKSRISI TRDTSKNQFF

LQLNSVTTED TATYYCARPY YYGIRGFAYW GQGTLVTVSA

GGGGSGGGGS GGGGSDIQMT QSPASLSASV GETVTITCRA

SENIYSYLAW YQQIQGKSPQ LLVYNSKTLA EGVPSRFSGS

GSGTQFSLKI NSLQPEDFGS YYCQHHYVTP YTFGGGTKLE

IKR
```

TABLE 8

Comparison of the binding kinetics for anti-human TC IgG
and scFv antibodies as measured by SPR (BIAcore).

| Antibody | Format | Antigen | $k_{on}$, $10^4$ (L mol$^{-1}$ s$^{-1}$) | $k_{off}$, $10^{-4}$ (s$^{-1}$) | Ka, $10^7$ (L mol$^{-1}$) |
|---|---|---|---|---|---|
| 3C4 | IgG1 | HoloTC | 3 | 24 | 1.3 |
| 3C4 | IgG1 | ApoTC | 0 | 0 | 0 |
| 3C4 | scFv | HoloTC | 0.6 | 24 | 0.3 |
| 3C4 | scFv | ApoTC | 0 | 0 | 0 |
| TC2 | IgG1 | HoloTC | 10 | 4 | 25 |
| TC2 | IgG1 | ApoTC | 10 | 15 | 7 |
| TC2 | scFv | HoloTC | 0.4 | 15 | 0.3 |
| TC2 | scFv | ApoTC | N/D | 15 | N/D |

$k_{on}$ = association rate constant (M$^{-1}$s$^{-1}$)
$k_{off}$ = disociation rate constant (s$^{-1}$)
Ka = kon/koff (M$^{-1}$)

EXAMPLE 12

Preparation of Single Chain Antibody Fragments from mRNA Using Commercial Methods 12.1). Preparation of mRNA Pure mRNA is prepared from hybridoma cells using the QuickPrep mRNA Purification Kit (Amersham Biosciences) and the protocol supplied therewith.

12.2). Conversion to cDNA

The mRNA is used as a template to prepare cDNA. Random hexamer primers are used to prime cDNA synthesis and generate a cDNA:mRNA heteroduplex using the First-Strand cDNA Synthesis kit (Amersham Biosciences) and supplied protocol.

12.3). PCR of Vy and VL Genes.

The cDNA:mRNA heteroduplex is heat denatured and the cDNA strand used as template for PCR, in the presence of specific primers designed for the amplification of $V_H$ and $V_L$ domains from the Light and Heavy Primer Mix (Amersham Biosciences). Alternatively, several such primers are given in the literature (e.g. from McCafferty, supra) and may be prepared by standard synthetic methods.

12.4). Purification of Amplified $V_H$ and $V_L$ Genes

The amplified $V_H$ and $V_L$ chain PCR fragments are purified separately by electrophoresis on a 2% low melting point agarose gel with ethidium bromide staining. The $V_H$ and $V_L$ bands are carefully excised and the PCR product recovered with S.N.A.P.™ Gel Purification Kit (Invitrogen, cat. no. K1999-25) or a similar commercial product.

12.5). Assembly of $V_H$ and TA Genes into scFv Genes

The $V_H$ and $V_L$ chain domains are linked together using the linker fragment (GGGS)$_3$ to give a complete scFv sequence. The linker is flexible enough to allow the $V_H$ and $V_L$ domains to maintain their antigen binding conformation and connects the $V_H$ and $V_L$ domains. Other linkers are well know and comprise around 15 amino acids.

12.6). PCR Amplification, Digestion, and Ligation To Phagemid

The scFv antibody is amplified using primers which incorporate sites for restriction enzymes (Sfi I and Not I (Promega)). The amplified DNA is purified as in I2.4 above, digested with these enzymes and finally subcloned into the phagemid pCANTAB-5E (Amersham Biosciences).

12.7 Transformation and Expression of Soluble Antibodies

The vector containing the scFv gene is introduced into *E. Coli* cells by electroporation and the cells grown under conditions that will allow only vector infected cells to grow. Preferably a strain of *E. Coli* is chosen that transports the synthesized protein into the periplasmic space (e.g. HB2151).

To simplify purification of the synthesized scFv antibody, the scFv gene in 12.6 may be subcloned into an expression vector inserting a "tag" at the C-terminus of the antibody (e.g. pCANTAB6; his-tag). The "tag" is recognized by a monoclonal antibody and may be used for affinity-chromatography purification.

12.8 Transformation and Expression of scFv Antibodies on the Surface of Bacteriophage The vector pCANTAB5E containing the scFv gene is introduced into a suppressor strain of *E. Coli* (e.g. TG1), which allows the scFv antibody to be displayed on the surface of the phage. Phage particles displaying scFv antibodies are prepared essentially as described in 4.2

EXAMPLE 13

Affinity Maturation of scFv 3C4 Using Phage Display

To construct a scFv library displayed on the surface of bacteriophage essentially the steps of Example 12 is followed but a PCR mutagenesis method is introduced at step 12.6. Several such methods are described but a non-localized mutagenesis strategy such as error-prone PCR (e.g. Genemorph® Random mutagenesis kit, Stratagene, USA) or chain-shuffling (e.g. Fragment Induced Diversity, FIND™, Alligator Bioscience AB, Sweden) to randomly introduce mutations throughout the V-genes is generally recommended. In the latter case, at least two different scFv antibody clones are required between which to shuffle the chains (Table 6). Biopanning of the mutant libraries is then performed to select clones of higher affinity.

13.1). Error-Prone PCR Amplification.

The scFv antibody DNA is PCR amplified using sequencing primers for antibody V genes and Taq polymerase, in the presence of 0.5-2.0 mM MnCl2, which reduces the fidelity of the Taq polymerase. The amplified DNA is purified, digested, and subcloned as described in Example 12.

13.2) Chain-Shuffling (FIND™, Alligator Bioscience AB)

At least two different scFv antibody DNA are fragmented with an exonuclease (e.g. BAL31; Fermentas Life Sciences, Lithuania) to generate populations of single stranded fragments. The ssDNA fragments are purified by phenol extraction/ethanol precipitation followed by electrophoresis as described in 12.4. The ssDNA fragments are reassembled and amplified by PCR using primer sequences that anneal to the 3' and 5' ends of the fragments. The annealed scFv are purified, and subcloned as described in Example 12.

13.3) Biopanning of Mutant Libraries.

The generated libraries were of size $10^5$-$10^6$ individual clones. Holo-TC was biotinylated as described in 6.6 and bound to streptavidin coated beads (Dynabeads®, Dynal Biotech, Norway). The biopanning procedure was performed essentially as described in 4.2. To assure that holoTC specificity was not compromised, the biopanning was carried out in the presence of at least a 100-fold excess of apoTC. Alternatively, libraries were pretreated with excess apoTC immobilized on magnetic beads.

13.4) Screening ELISA

Individual phage antibody clones were screened by ELISA essentially as described in 4.3, using holoTC coated microtiter plates. The plates were prepared by binding biotinylated holoTC onto streptavidin coated microtiter wells (NUNC™, Denmark). Selected phage antibodies were transformed and expressed as soluble scFv antibodies, as described in 12.7.

13.5) Evaluation of Selected scFv Antibodies

Selected scFv antibodies were evaluated by surface plasmon resonance essentially as described in Example 2. Purified antibody preparations were injected over a chip with immobilized holoTC. The holoTC chip was prepared by binding holoTC to a chip prepared as described in 2.1 or by binding biotinylated holoTC on a streptavidin coated SA chip (Biacore, Sweden). The results obtained are shown in Tables 9 and 10.

TABLE 9

Affinity measurements of mutated scFv 3C4 from first round of library constructions.

| Clone | Sequence* | koff | kon | KD |
|---|---|---|---|---|
| 3.10E5 | P14S, A34T, A97V, R159L | 2.9E-04 | 1.2E+04 | 2.4E-08 |
| 2.7G5 | A34T, T87S, S200N, G201R | 2.3E-04 | 9.1E+03 | 2.6E-08 |
| 3.7D9 | A34T, F41L | 3.1E-04 | 9.5E+03 | 3.2E-08 |
| 3.3D7 | A34T, S198N | 4.8E-04 | 8.7E+03 | 5.5E-08 |
| 2.10H3 | A34V, L46M | 5.0E-04 | 8E+03 | 6.2E-08 |
| 2.9A11 | A34T | 3.6E-04 | 5.3E+03 | 6.9E-08 |
| 3.10D1* | A34T**, S53N | 6.4E-04 | 5.1E+03 | 7.1E-08 |
| 3.2H8 | A34T, T232R | 4.8E-04 | 6.0E+03 | 8.0E-08 |
| 3.7C10 | A34V | 5.6E-04 | 7.0E+03 | 8.0E-08 |
| 3.9G2 | Q16L, T30A, A34T, A190T | 5.9E-04 | 3.8E+03 | 1.5E-07 |
| 3.9D1 | G8V, A34T, S147Y | 6.6E-04 | 1.8E+03 | 3.7E-07 |
| 3.10H8 | A34T, E216G | 9.0E-04 | 2.2E+03 | 4.0E-07 |
| 2.4F10 | wt | 3.10E-03 | 6.4E+03 | 4.9E-07 |

*Shows substitutions in the sequence given in Table 7.
wt, wild type, i.e. nonmutated scFv 3C4.
kon = association rate constant ($M^{-1}s^{-1}$)
koff = disociation rate constant ($s^{-1}$)
KD = koff/kon (M)
Bold - substitution in complimentarity determining region (CDR).

TABLE 10

Affinity measurements of mutated scFv 3C4 from second round of library constructions.

| Clone name | Sequence* | koff |
|---|---|---|
| F1.3E4 | P14S, A34T | 3.30E-04 |
| F1.3H8 | P14S, A34T, A97V | 4.10E-04 |
| F1.3E5 | P14S, A34T, S53N, L115P | 4.40E-04 |
| F1.8D9 | P14S, A34T, T87S, R159L | 4.50E-04 |
| F1.7E7 | P14S, A34T, A97V, V193A | 6.04E-04 |
| F1.8C12 | P14S, A34T, A97V, L115P, G128D, R159L | 6.10E-04 |
| 3.10E5 | P14S, A34T, A97V, R159L | 6.50E-04 |
| F1.8C10 | A34T, T87S, A97V, A144V, K177I, S186A | 7.20E-04 |
| F1.9C4 | A34T, N84Y, A97V, S200N, G201R | 7.70E-04 |

*Shows substitutions in the sequence given in Table 7.
Bold italic - new amino acid changes compared to Table 9

The koff values reported are generally higher than those of Table 9 because the amount of bound antigen was lower in this experiment, 500RU as compared to 3500RU, and thus less rebinding occurred.

EXAMPLE 14

Reconfiguration of scFv Antibodies Back into Full Length Antibody Format

The scFv antibody fragments are reconfigured back to full length antibody format by joining the scFv from cDNA clones to mouse or human genomic constant regions using standard recombinant DNA techniques (e.g. McCafferty J, Hoogenboom H R, and Chiswell D J (ed.) (1996) *Antibody Engineering—A practical approach*, IRL Press, Oxford, UK). The chimaeric heavy and light chain immunoglobulin genes are placed under the control of a strong viral promotor (e.g. hCMV-MIE), and cotransfected into cell line COS-1 (ATCC#CRL1650) or myeloma cell line NS0 (ATCC#85110503), for transient and stable expression of antibody, respectively. To minimize risk of interfering autoantibodies against mammalian IgG Fc (e.g. rheumatoid factor), reconfiguration may be performed into the IgG3 format, which is less susceptible to such autoantibodies.

14.1) Transfection of COS-1 Cells

The COS-1 cells are plated out on a Petri dish the day before transfection. Plasmid DNA, containing the gene to be expressed, are transfected into the cells using e.g. Eugene 6 (Roche) and antibody harvested from the medium after 3 days.

14.2) Transfection of NS0 Cells

Plasmid DNA are transfected into about 10E7 NS0 cells on ice by electroporation. Cells are then grown in selective medium allowing only transfected cells to survive. Antibody is harvested from cell medium three weeks post-transfection.

EXAMPLE 15

Epitope Mapping of Aptamer b974-3t1

The epitope specificity of 18,000 Da aptamer b974-3t1 was determined.

15.1 Binding of Aptamer to holoTC Immobilised on Various Anti-humanTC mAbs

An array of 10 different anti-human TC antibodies were immobilised onto a dextran coated chip which had been pre-coated with rabbit anti-mouse IgGs. The procedure was as described above for Example 2.2. HoloTC (15 µl, 0.4 µM)

was injected and allowed to bind to the mAb, followed by aptamer b974-3t1 15 μl, 1 μM).

15.2 Binding of holoTC by Immobilised Aptamer in the Presence and Absence of Various Anti-HumanTC mAbs Aptamer b974-3t1 was immobilised on strepatvidin coated magnetic particles (0.8 μm) in a method analagous to Example 3.1 above, substituting streptavidin particles for the anti-mouse IgG coated particles of that Example. The particles were then allowed to capture native holoTC as described in Example 3.2 above, in the presence of 9 different TC specific antibodies. All antibodies were present at 10 μg/ml except for 5H2 and 3C4 which were tested at 100 μg/ml.

TABLE 11

Binding of aptamer to holoTC immobilised on various mAbs and binding of holoTC to immobilised aptamer in the presence of various mAbs

| Epitope | mAb | Binding of: | | |
|---|---|---|---|---|
| | | aptamer to holoTC captured by mAb (mRU/RU) | holoTC to aptamer in presence of mAb (% of w/o mAb) | Overlap + small ++ medium +++ full |
| 1 | 3-9 | 135 | 7 | + |
| 2A | 2-2 | 0 | n.d. | +++ |
| 2A | 3-11 | 0 | 3 | +++ |
| 2A | TC7 | 0 | 3 | +++ |
| 2B | 5H2 | 0 | 41 | ++ |
| 2B | 4-7 | 88 | 54 | ++ |
| 3 | TC4 | 104 | 100 | + |
| 4 | 3C4 | 39 | 60 | ++ |
| 5 | TC2 | 97 | 69 | ++ |
| 6 | 3C12 | 0 | 3 | +++ |

As seen in Table 11, aptamer b974-3t1 overlapped completely or almost completely with epitope 6 antibodies and with some epitope 2 antibodies (2A). Ambiguous results were obtained with mAb 3-9 and to some extent with 5H2; the aptamer and the mAb both bound simultaneously to holoTC in one setting but not in the other, however, it is not unusual for the mode of presentation to affect binding efficiency. Since simultaneous binding was seen in at least one experiment, complete overlap is excluded.

Figure 10:
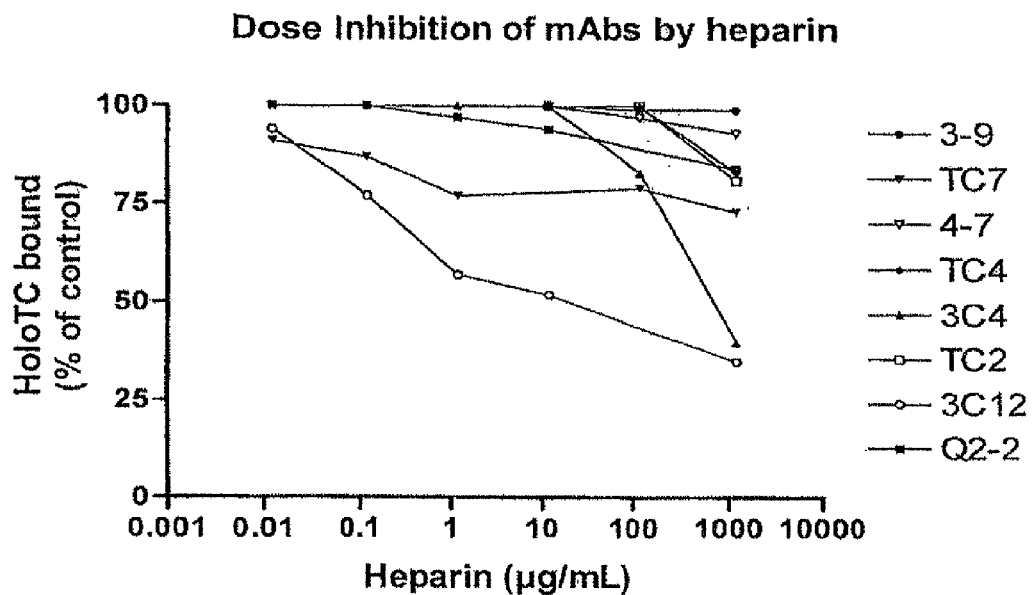
FIG. 10 represents the inhibition of binding between TC and various of the mAbs described herein caused by the polysaccharide heparin at various concentrations.

In line with the strong overlap of the aptamer with epitope 6, the overlap with heparin is also very strong (see FIG. 3 for epitope map and FIG. 10 for inhibition data).

EXAMPLE 16

Capture of holoTC by holoTC Specific Antibody 3C4 and Detection by Aptamer b974-3t1

Figure 11:
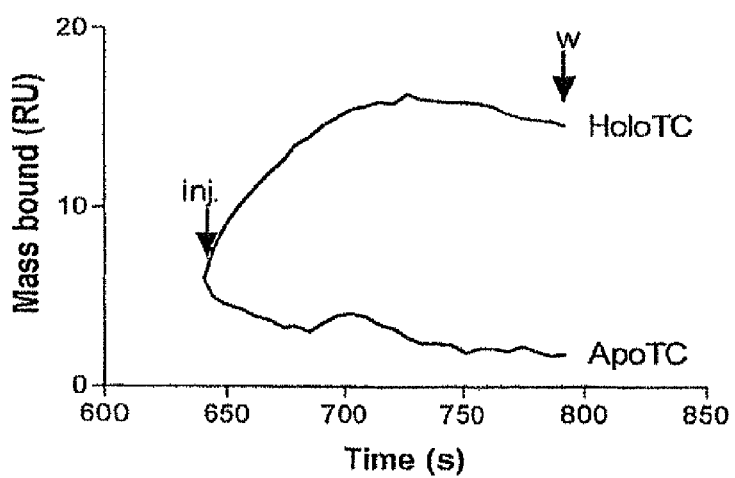
FIG. 11 represents an SPR "sensorgram" showing the binding of aptamer b974-3t1 to holoTC immobilised to a chip by mAb 3C4 (top line). No response is seen (bottom line) when apo-TC is used in place of holo-TC because mAb 3C4 does not recognise (and therefore does not capture) apo-TC.

The binding events were followed in real time using surface plasmon resonance and performed on a Biacore instnnn-bnt (Biacore™, Sweden). Monoclonal antibody 3C4 was immobilized on a dextran coated CM5 chip, as described in Example 2.1 above. The chip with immobilized antibody was introduced into the instrument, after which was injected 15 μL of 0.4 M holoTC or apoTC and subsequently 15 μL of 1 μM aptamer b974-3t1. The aptamer bound to a level of about 10 RU to the captured holoTC; 39 mRU of aptamer bound per RU of holoTC captured (FIG. 11, upper curve). As no apoTC was captured by the holoTC specific mAb 3C4, no aptamer bound either in this second case (FIG. 11, lower curve).

EXAMPLE 17

Capture of apoTC and holoTC by Immobilized TC-Specific Aptamer b974-3t1 and Detection of Bound holoTC using mAb 3C4 and Total TC (apoTC and holoTC) by Epitope 2 Antibody, mAb 4-7

17.1 Immobilization of Aptamer on Streptavidin Coated SA Chip

Biotinylated aptamer b974-3t1 was immobilized on a streptavidin coated SA chip (Biacore, Sweden). The aptamer was diluted to about 18 ng/ml in 0.01 M HEPES buffer, pH 7.4, 0.15 M NaCl, 0.005% (v/v) surfactant P20 supplemented with 2 mM CaCl2 and 2 mM MgCl$_2$ (HBS-P+) and injected over the chip at 5 μL/min for 7 min. The binding of aptamer was followed in real time and the amount of mass bound was recorded in RU (response units) in the sensorgram. The aptamer was immobilized on the chip to about 1500 RU.

17.2 Binding of apoTC and holoTC to Immobilized Aptamer

ApoTC and holoTC were diluted in HBS-P+ to about 18 ng/mL and injected over the chip with the immobilized aptamer at 5 μL/min for 7 min. The amount of mass bound was recorded in the sensorgram.

17.3 Detection of Bound apoTC and holoTC by Monoclonal Antibodies Specific for TC and holoTC Monoclonal antibody mAb 3C4, specific for holoTC, diluted to 50 ng/mL in HBS-P+ was injected over the chip with captured apoTC or holoTC at 5 μL/min for 1 min. Thereafter a monoclonal antibody with specificity for TC but without holoTC specificity and with an epitope non-overlapping with mAb 3C4 (epitope 2 antibody; mAb 4-7) was injected at 5 μL/min for 1 min. The mass bound of each mAb was recorded in the sensorgram.

Figure 12:
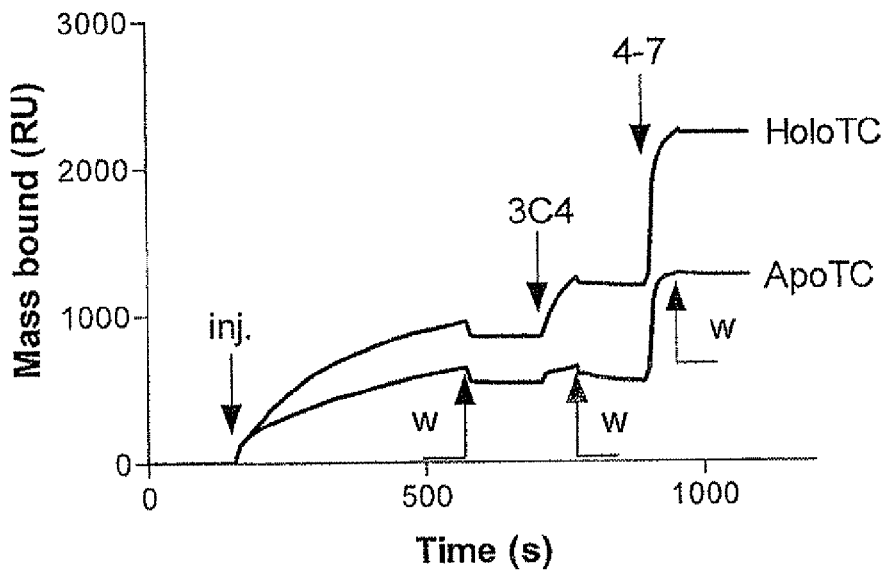
FIG. 12 represents the sequential binding of antibodies specific for epitope 4 (3C4) and epitope 2B (4-7) to holo-TC and apo-TC captured by aptamer b974-3t1 (down arrows indicate time of injections). No response is seen when 3C4 is injected over captured apo-TC because epitope 4 is not present.

FIG. 12 depicts a typical sensorgram showing capture of apoTC and holoTC by the immobilized aptamer, followed by binding of mabs 3C4 and 4-7 to the captured TC. The arrows identify injections of TC (inj.), mAb 3C4 (3C4) and mAb 4-7 (4-7), and wash (w). Whereas mAb 3C4 bound only to captured holoTC, mAb 4-7 bound equally well to apoTC and holoTC (Table 12). As shown in FIG. 12, aptamer b974-3t1 exhibited a slight specificity for holoTC over apoTC (i.e, the amount of TC bound to the chip was greater when it was in the holo form). The preference was estimated to be about 3-fold.

TABLE 12

Binding of mAbs 3C4 and 4-7 to apoTC and holoTC captured by aptamer b974-3t1

| TC | Bound mAb 3C4* (%) | Bound mAb 4-7* (%) |
|---|---|---|
| ApoTC | 0 | 104 |
| HoloTC | 39 | 106 |

*Results expressed relative to amount of TC captured.

EXAMPLE 18

Ab Initio Prediction of Human Transcobalamin 3D Structure

The simulation was performed using the HMMSTR/Rosetta prediction server. The HMMSTR/Rosetta server predicts the structure of proteins from the sequence: secondary structure in the form of 3-states (H,E,L), local structure in the form of backbone torsion angles (phi,psi), supersecondary structure in the form of context symbols (for strands and beta turns), and tertiary structure in the form of coordinates. (C. Bystoff, V. Thorsson, D. Baker) HMMSTR is a hidden Markov model based on the I-sites Library of sequence-structure motifs. 1-sites predicts local structure motifs in the query, and these are then used by Rosetta to generate the 3D structure. Rosetta is a Monte Carlo Fragment Insertion protein folding program developed by Kim Simons, David Baker, Ingo Rudzinski and Charles Kooperberg (Simons et al, 1997). The amino acid sequence of human transcobalamin was taken from Swissprot ID no. P20062.

Figure 13A:
FIG. 13a represents the structure of human TC showing epitope 4.
Figure 13B:
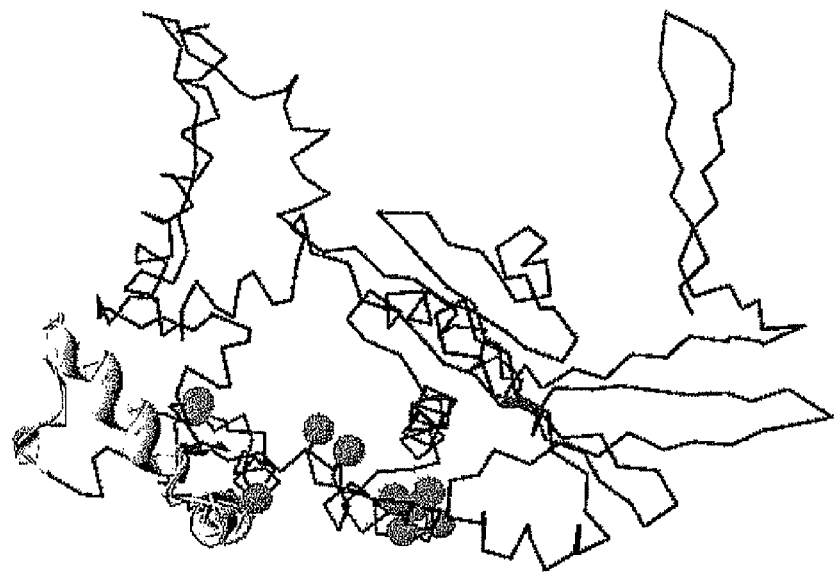
FIG. 13b represents the structure of human TC showing the heparin binding site.

FIG. 13 shows the predicted 3D structure of apotranscobalamin with the deletion mutation (see Example 2.4) in ribbon format. Upper FIG. 13 shows the front of TC with the mAb 3C4 epitope (from Example 19) depicted as rose spheres. Lower FIG. 13 shows the back of TC with the tentative heparin binding site depicted as spheres.

The predicted spatial proximity of the 27 amino acid deletion and the putative heparin binding site is corroborated by our experimental finding (Examples 2 and 13) that antibodies to epitope 2, which overlap with the deletion mutation, are inhibited by heparin and aptamer b974-3t1, which both bind to the heparin binding site. Furthermore, because antibodies to epitope 6 are inhibited by heparin and aptamer b974-3t1 and to some extent by epitope 1 and 2 antibodies, the 3D structure indicates that epitope 6 straddles the heparin binding site.

Figure 14:
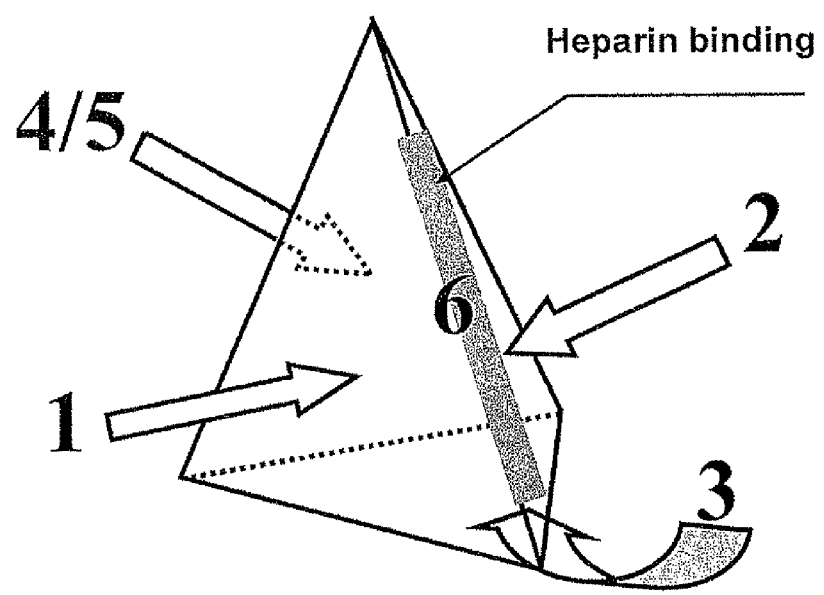
FIG. 14 shows a schematic of the various epitopes identified on holoTC.

FIG. 14 shows a cartoon of the holoTC structure as a three sided pyramid and depicting the localization of different antibody epitopes based on experimental data.

EXAMPLE 19

Ab Initio Prediction of the Epitope of mAb 3C4 on holoTC

Simulations of the docking of cobalamin with apoTC and the docking of mAb 3C4 with holoTC were performed by Cambridge Proteomics Ltd using their proprietary simulation technology. The amino acid sequence of apotranscobalamin was taken from Swissprot ID no. P20062. The chain was initially shaped randomly. The disulfides known to be formed between cysteines 21 and 267, 83 and 96, 116 and 309, and 165 and 205 (S N Fedosov et al, J Biol Chem 1999; 274: 26015-20) were programmed to be created when the sulfurs in the respective cysteine residues approached a distance of 2.038±0.05 Å. The 3D cobalamin structure was taken from the PDB entry IBMT (methionine synthase B12 binding regions) and relaxed in water before reacting with TC. As reported in the literature, cobalamin binding caused significant structural changes in TC (E Hippe, Biochem Biophys Acta 1970; 208:337-9).

As we had only determined the amino acid sequence of the CDR region of mAb 3C4 (Table 7) the initial structure was based on the mAb 3C4 CDR sequence inserted into the human IgGI model (E A Padlan, Mol Immunol 1994;31:169-217). The variable regions were initially shaped randomly.

When simulating the interaction between mAb 3C4 and holoTC, the initial orientation was chosen randomly, with the binding region of the antibody pointing between the C165-C205 loop and the C-terminal end (320-427) of holoTC. The initial distance between antibody and holoTC was over 10A and the ionic strength of the solution was set at 50.

All simulations were run on a Linux work station running on Intel Xeon processors.

The epitope was defined as those amino acids in holoTC, which in the predicted complex are localized <5 Å from amino acids in the antibody, 36 amino acids fulfilled these requirements, and can be organized into three discrete regions spanning amino acids 39-77 plus 265-269, 161-243, and 271-297 (Table 13A). Including adjacent amino acids, the number of amino acid residues defining the epitope is 68 (Table 13B). The epitope is localized around a tunnel in the protein (FIG. 13). On the other side of the tunnel cobalamin is bound.

In the antibody, the amino acids corresponding to the epitope and the extended epitope were 32 and 39, respectively, constituting the paratope and the extended paratope. The amino acids are organized in two regions, 14 and 16 residues in the VL chain and 18 and 23 residues in the VH chain for the paratope and the extended paratope, respectively (Tables 14A and B).

Figure 15A:
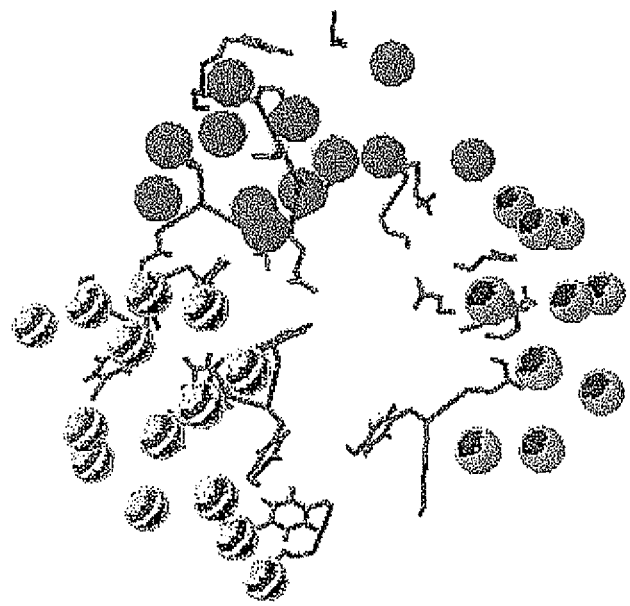
FIG. 15a represents the interaction between the paratope of 3C4 and the preferred epitope regions of holoTC.
Figure 15B:
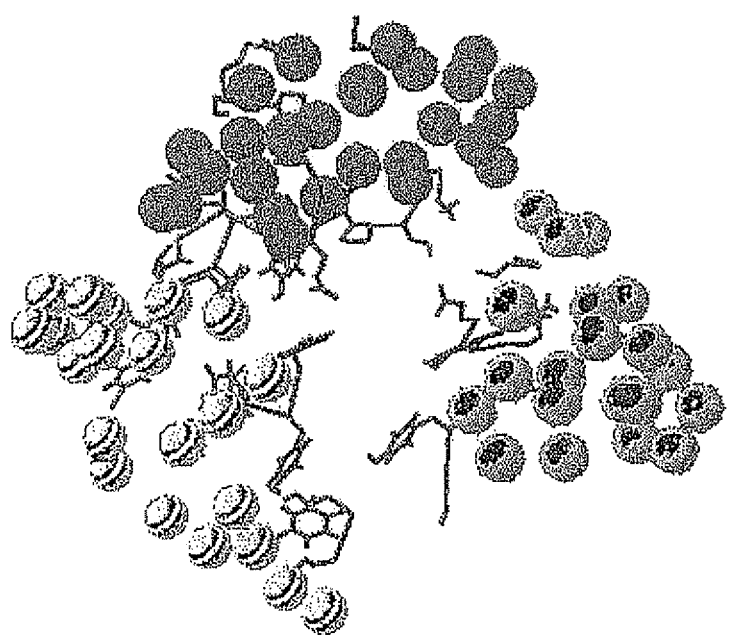
FIG. 15b represents the interaction between the extended paratope of 3C4 and the epitope regions of holoTC.

The interaction between the paratope (antibody) and the epitope (holoTC) and involved residues is depicted in FIG. 15A. The corresponding interaction between the extended paratope and extended epitope is depicted in FIG. 15B.

TABLE 13A

| Epitope residues | |
| --- | --- |
| Amino acid region | Amino acids |
| 39-77, 265-269 | L39, M42, N51, P52, I54, Q64, A65, E69, L73, L76, K77, T265, A266, K269 |
| 161-243 | I161, H172, V176, L180, T195, A196, R208, H239, N242, V243 |
| 271-296 | R271, V272, A273, L274, A276, Q279, Q284, M288, L293, P294, V295, L296 |

TABLE 13B

| Extended epitope | |
| --- | --- |
| Amino acid region | Amino acids |
| 39-77, 265-269 | L39, M42, L50, N51, P52, S53, I54, Q64, A65, E69, D70, L71, Y72, L73, H74, S75, L76, K77, T265, A266, K269 |
| 161-243 | I161, H172, D173, S174, V175, V176, D177, K178, L179, L180, Y181, A182, V183, E184, T195, A196, R208, H239, N242, V243 |
| 271-296 | R271, V272, A273, L274, L275, A276, S277, L278, Q279, D280, G281, A282, F283, Q284, N285, A286, L287, M288, I289, S290, Q291, L292, L293, P294, V295, L296, N297 |

TABLE 14A

| Paratope residues. | |
| --- | --- |
| Chain | Amino acids |
| VL | E1, Q3, Q5, T25, G26, Y27, S28, Y54, S55, Y100, Y101, Y102, R105, Q112 |
| VH | S31, Y32, K42, S43, Q45, L46, Y49, N50, T53, L54, E56, G57, V58, P59, S60, R61, E81 |

TABLE 14B

| Extended paratope | |
| --- | --- |
| Chain | Amino acids |
| VL | E1, V2, Q3, Q5, T25, G26, Y27, S28, S53, Y54, S55, Y100, Y101, Y102, R105, Q112 |
| VH | S31, Y32, L33, A34, W35, K36, K42, S43, P44, Q45, L46, Y49, N50, T53, L54, E56, G57, V58, P59, S60, R61, E81 |

The invention claimed is:

1. An assay method for assaying for holoTC in a sample, said method comprising contacting said sample with a specific binding partner for holoTC and detecting the resultant conjugates of holoTC and the specific binding partner, wherein:
said specific binding partner is a specific binding partner for holoTC having a specificity for holoTC over apoTC of at least 40-fold, and
said specific binding partner also has affinity for at least one constrained peptide comprising the motif SFFYS-LCYCW (SEQ ID NO: 9), relative to apoTC of at least 40-fold.

2. The method of claim 1, wherein said specific binding partner binds to at least one point in at least one of the regions I, II or III of human TC;
I) Leu 39 to Lys 77 and Thr 265 to Lys 269
II) Ile 161 to Val 243
III) Arg 271 to Asp 297.

3. The method of claim 1, wherein the binding of said specific binding partner to holoTC is blocked by a specific biding partner for an overlapping site on both holoTC and apoTC.

4. The method of claim 1, wherein said specific binding partner is an antibody, a single chain antibody, and antibody fragment or an antibody construct.

5. The method of claim 1, wherein said conjugates of holoTC and the specific binding partner are detected directly by means of a property of the conjugate.

6. The method of claim 1 wherein said conjugates of holoTC and the specific binding partner are detected indirectly by detecting further conjugates formed in competition or by detecting a conjugate of the specific binding partner, holoTC and a further ligand.

7. The method of claim 1, wherein said specific binding partner for holoTC is immobilised or immobilisable and is used to capture holoTC.

8. The method of claim 1, wherein said specific binding partner for holoTC is used to detect holoTC which is captured by an immobilised or immobilisable secondary ligand.

9. The method of claim 1 comprising the use of a constrained peptide mimotope comprising the motif SFFYS-LCYCW (SEQ ID NO: 9) or a construct of two or more such mimotopes.

10. The method of claim 9, wherein said mimotope is used as a competitior for holoTC in binding to said specific binding partner for holoTC.

11. The method of claim 1 comprising
i) contacting a liquid sample from a subject with an immobilised or immobilisable specific binding partner for holoTC whereby to form a holoTC:sbp conjugate,
ii) contacting the specific binding partner with a secondary ligand for TC or holoTC such that the secondary ligand binds to the bound holoTC to form a sbp:holoTC:secondary ligand conjugate;
iii) separating the unbound secondary ligand from the sbp: holoTC; secondary ligand conjugate;
iv) optionally releasing the holoTC:sbp:secondary ligand conjugate from being immobilised and/or releasing a holoTC:secondary ligand conjugate from the sbp;
v) optionally adding a cosubstrate or tertiary ligand to facilitate detection of the holoTC:sbp:secondary ligand conjugate or a holoTC:secondary ligand conjugate;
vi) detecting holoTC:sbp:secondary ligand conjugate or a holoTC:secondary ligand conjugate; and
vii) relating the detected amount of holoTC:sbp:secondary ligand conjugate to the concentration of holoTC in the liquid sample to provide a measurement of the holoTC present in the liquid sample.

12. The method of claim 11 further comprising relating the concentration of holoTC present in the liquid sample to the presence or absence of cobalamin deficiency in the subject.

13. The method of claim 1 additionally comprising measuring apoTC or total TC.

* * * * *